US 7,132,588 B2

(12) United States Patent
Fitzmaurice et al.

(10) Patent No.: US 7,132,588 B2
(45) Date of Patent: *Nov. 7, 2006

(54) VIRAL EXPRESSION VECTORS

(75) Inventors: Wayne P. Fitzmaurice, Vacaville, CA (US); Gregory P. Pogue, Vacaville, CA (US); John A. Lindbo, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 496 days.

This patent is subject to a terminal disclaimer.

(21) Appl. No.: 10/624,193

(22) Filed: Jul. 21, 2003

(65) Prior Publication Data

US 2005/0175590 A1    Aug. 11, 2005

Related U.S. Application Data

(63) Continuation of application No. 09/565,616, filed on May 4, 2000, now Pat. No. 6,656,726.

(60) Provisional application No. 60/132,697, filed on May 4, 1999.

(51) Int. Cl.
*A01H 1/00*      (2006.01)
*A01H 11/00*     (2006.01)
*C12N 15/05*     (2006.01)
*C07H 21/02*     (2006.01)
*C07H 21/04*     (2006.01)

(52) U.S. Cl. .................. 800/278; 800/277; 800/295; 536/23.1; 536/23.4

(58) Field of Classification Search .................. None
See application file for complete search history.

(56) References Cited

U.S. PATENT DOCUMENTS

| | | | |
|---|---|---|---|
| 5,316,931 A | 5/1994 | Donson et al. | 435/172.3 |
| 5,405,783 A | 4/1995 | Pirrung et al. | 436/518 |
| 5,412,087 A | 5/1995 | McGall et al. | 536/24.3 |
| 5,445,934 A | 8/1995 | Fodor et al. | 435/6 |
| 5,695,937 A | 12/1997 | Kinzler et al. | 435/6 |
| 5,816,653 A | 10/1998 | Benson | 297/284.4 |
| 5,866,785 A | 2/1999 | Donson et al. | 800/205 |
| 5,889,190 A | 3/1999 | Donson et al. | 800/288 |
| 5,889,191 A | 3/1999 | Turpen | 800/288 |
| 5,977,438 A | 11/1999 | Turpen et al. | 800/288 |

FOREIGN PATENT DOCUMENTS

| | | |
|---|---|---|
| WO | WO 95/21248 | 10/1995 |
| WO | WO 00/66743 | 9/2000 |

OTHER PUBLICATIONS

Viaplana et al., Transient Expression of a GUS Reporter Gene from Cauliflower Mosaic Virus . . . , Journal of General Virology, 2001, vol. 82, pp. 59-65.

Porta et al., Use of Viral Replicons for the Expression of Genes in Plants, Molecular Biotechnology, 1996, vol. 5, pp. 209-221.

Ausubel, F.M., et al., Current Protocols in Molecular Biology—vol. 1 (1987).

Callis, J et al., "Introns increase gene expression in cultured maize cells," *Genes and Development*, 1:1183-1200 (1987).

Dawson, William and Krisi Lehto, "Regulation of Tobamovirus Gene Expression," *Advances in Virus Research* 38:307-342 (1991).

Donson, J., et al., "Agrobacterium-Mediated Infectivity of Cloned Digitaria Streak Virus DNA," *Virology* 162:248-250 (1988).

Epel, B., et al., "Plant virus movement protein dynamics probed with GFP-protein fusion," GENE vol. 173(1):75-79 (1996).

Fraley, R., et al., "Expression of bacterial genes in plant cells," *Proc. Natl. Acad. Sci. U.S.A.*, 80:4803-4807 (1983).

Freshney, R.I., ed., *Animal Cell Culture: a practical approach* (1987).

Fromm, M., et al., "Stable transformation of maize after gene transfer by electroporation," *Nature* 319:791-793 (1986).

Gardner, R., et al., "Potato spindle tuber viroid infections mediated by the Ti plasmid of *Agrobacterium tumefaciens*," Plant Mol. Biol. 6:221-228 (1986).

Harlow, Ed and David Lane, eds., Antibodies, a Laboratory Manual, Cold Spring Harbor Laboratory (1988).

Lazarowitz, S., "Infectivity and complete nucleotide sequence of the genome of a South African isolate of maize streak virus," *Nucl. Acids Res*. 16(1):229-249 (1988).

Lewandowski, D and Willan O. Dawson., "Functions of the 126- and 183-kDA Proteins of Tobacco Mosaic Virus," *Virology* 271:90-98 (2000).

Matthews, R.E.F., *Plant Virology*, 3rd edition (1991).

McPherson, M.J., B.D. Hames and G.R. Taylor eds, the series *Methods in Enzymology* (Academic Press, Inc.): *PCR 2: a Practical Approach* (1995).

Potrykus, I., et al., "Molecular and general genetics of a hybrid foreign gene introduced into tobacco by direct gene transfer," *Mol. Gen. Genet*., 199:169-177 (1985).

Sambrook, J. , E.F. Fritsch and T. Maniatis., *Molecular Cloning: A Laboratory Manual*, 2nd edition, Cold Spring Harbor Laboratory Press (1989).

Sanford, J.C. et al. , "Optimizing the Biolistic Process for Different Biological Applications," *Methods in Enzymology*, 217:483-509 (1993).

(Continued)

*Primary Examiner*—Joseph Woitach
(74) *Attorney, Agent, or Firm*—Thomas R. Gallegos; Wayne P. FitzMaurice

(57) ABSTRACT

The present invention provides nucleic acid sequences having an altered viral movement protein and 126/183 kDa replicase proteins further characterized in its ability tostabilize a transgene contained in a virus that expresses the altered movement protein. The present invention also provides viral vectors expressing the altered movement protein, cells transformed with the vectors, and host plants infected by the viral vectors.

12 Claims, 17 Drawing Sheets

OTHER PUBLICATIONS

Sijen, T., et al., "RNA-mediated virus resistance: Role of repeated transgenes and delineation of targeted regions," The Plant Cell, vol. 8(12): 227-2294 (1996).

Zhou, Guang-Yu., et al., "Introduction of Exogenous DNA into Cotton Embryos," Methods in Enzymology, 101:433-481 (1983).

"Methods for Plant Molecular Biology," A. Weissbach and H. Weissbach, eds., Academic Press, Inc., San Diego, Calif. (1988).

```
1037    ATGGCTCTAGTTGTTAAAGGAAAAGTGAATATCAATGAGTTTATCGACCT
1057    ATGGCTCTAGTTGTTAAAGGAAAAGTGAATATCAATGAGTTTATCGACCT
        **************************************************

1037    GACAAAAATGGAGAAGATCTTACCGTCGATGTTTACCCCTGTAAAGAGTG
1057    GACAAAAATGGAGAAGATCTTACCGTCGATGTTTACCCCTGTAAAGAGTG
        **************************************************

1037    TTATGTGTTCCAAAGTTGATAAAATAATGGTTCATGAGAATGAGTCATTG
1057    TTATGTGTTCCAAAGTTGATAAAATAATGGTTCATGAGAATGAGTCATTG
        **************************************************

1037    TCAGGGGTGAACCTTCTTAAAGGAGTTAAGCTTATTGATAGTGGATACGT
1057    TCAGGGGTGAACCTTCTTAAAGGAGTTAAGCTTATTGATAGTGGATACGT
        **************************************************

1037    CTGTTTAGCCGGTTTGGTCGTCACGGGCGAGTGGAACTTGCCTGACAATT
1057    CTGTTTAGCCGGTTTGGTCGTCACGGGCGAGTGGAACTTGCCTGACAATT
        **************************************************

1037    GCAGAGGAGGTGTGAGCGTGTGTCTGGTGGACAAAAGGATGGAAAGAGCC
1057    GCAGAGGAGGTGTGAGCGTGTGTCTGGTGGACAAAAGGATGGAAAGAGCC
        **************************************************

1037    GACGAGGCCACTCTCGGATCTTACTACACAGCAGCTGCAAAGAAAAGATT
1057    GACGAGGCCATTCTCGGATCTTACTACACAGCAGCTGCAAAGAAAAGATT
        **********  **************************************

1037    TCAGTTCAAGGTCGTTCCCAATTATGCTATAACCACCCAGGACGCGATGA
1057    TCAGTTCAAGGTCGTTCCCAATTATGCTATAACCACCCAGGACGCGATGA
        **************************************************

1037    AAAACGTCTGGCAAGTTTTAGTTAATATTAGAAATGTGAAGATGTCAGCG
1057    GAAACGTCTGGCAAGTTTTAGTTAATATTAGAAATGTGAAGATGTCAGCG
         *************************************************

1037    GGTTTCTGTCCGCTTTCTCTGGAGTTTGTGTCGGTGTGTATTGTTTATAG
1057    GGTTTCTGTCCGCTTTCTCTGGAGTTTGTGTCGGTGTGTATTGTTTATAG
        **************************************************

1037    AAATAATATAAAATTAGGTTTGAGAGAGAAGATTACAAACGTGAGAGACG
1057    AAATAATATAAAATTAGGTTTGAGAGAGAAGATTACAAACGTGAGAGACG
        **************************************************

1037    GAGGGCCCATGGAACTTACAGAAGAAGTCGTTGATGAGTTCATGGAAGAT
1057    GAGGGCCCATGGAACTTACAGAAGAAGTCGTTGATGAGTTCATGGAAGAT
        **************************************************

1037    GTCCCTATGTCGATCAGGCTTGCAAAGTTTCGATCTCGAACCGGAAAAAA
1057    GTCCCTATGTCGATCAGGCTTGCAAAGTTTCGATCTCGAACCGGAAAAAA
        **************************************************
```

Figure 1a

```
1037        GAGTGATGTCCGCAAAGGGAAAAATAGTAGTAGTGATCGGTCAGTGCCGA
1057        GAGTGATGTCCGCAAAGGGAAAAATAGTAGTAGTGATCGGTCAGTGCCGA
            **************************************************

1037        ACAAGAACTATAGAAATGTTAAGGATTTTGGAGGAATGAGTTTTAAAAAG
1057        ACAAGAACTATAGAAATGTTAAGGATTTTGGAGGAATGAGTTTTAAAAAG
            **************************************************

1037        AATAATTTAATCGATGATGATTCGGAGGCTACTGTCGCCGAATCGGATTC
1057        AATAATTTAATCGATGATGATTCGGAGGCTACTGTCGCCGAATCGGATTC
            **************************************************

1037        GTTTTAA
1057        GTTTTAA
            *******
```

Figure 1b

| | |
|---|---|
| 1037 | MALVVKGKVNINEFIDLTKMEKILPSMFTPVKSVMCSKVDKIMVHENESL |
| 1057 | MALVVKGKVNINEFIDLTKMEKILPSMFTPVKSVMCSKVDKIMVHENESL |
| | ************************************************* |
| 1037 | SGVNLLKGVKLIDSGYVCLAGLVVTGEWNLPDNCRGGVSVCLVDKRMERA |
| 1057 | SGVNLLKGVKLIDSGYVCLAGLVVTGEWNLPDNCRGGVSVCLVDKRMERA |
| | ************************************************* |
| 1037 | DEATLGSYYTAAAKKRFQFKVVPNYAITTQDAMKNVWQVLVNIRNVKMSA |
| 1057 | DEAILGSYYTAAAKKRFQFKVVPNYAITTQDAMRNVWQVLVNIRNVKMSA |
| | *** ****************************  **************** |
| 1037 | GFCPLSLEFVSVCIVYRNNIKLGLREKITNVRDGGPMELTEEVVDEFMED |
| 1057 | GFCPLSLEFVSVCIVYRNNIKLGLREKITNVRDGGPMELTEEVVDEFMED |
| | ************************************************* |
| 1037 | VPMSIRLAKFRSRTGKKSDVRKGKNSSSDRSVPNKNYRNVKDFGGMSFKK |
| 1057 | VPMSIRLAKFRSRTGKKSDVRKGKNSSSDRSVPNKNYRNVKDFGGMSFKK |
| | ************************************************* |
| 1037 | NNLIDDDSEATVAESDSF |
| 1057 | NNLIDDDSEATVAESDSF |
| | ****************** |

Figure 2

Complete sequence of BSG 1037 (SEQ ID NO.: 1)

GTATTTTTACAACAATTACCAACAACAACAAACAACAGACAACATTACAATTACTAT
TTACAATTACAATGGCATACACA
CAGACAGCTACCACATCAGCTTTGCTGGACACTGTCCGAGGAAACAACTCCTTGGTC
AATGATCTAGCAAAGCGTCGTCT
TTACGACACAGCGGTTGAAGAGTTTAACGCTCGTGACCGCAGGCCCAAGGTGAACT
TTTCAAAAGTAATAAGCGAGGAGC
AGACGCTTATTGCTACCCGGGCGTATCCAGAATTCCAAATTACATTTTATAACACGC
AAAATGCCGTGCATTCGCTTGCA
GGTGGATTGCGATCTTTAgAACTGGAATATCTGATGATGCAAATTCCCTACGGATCA
TTGACTTATGACATAGGCGGGAA
TTTTGCATCGCATCTGTTCAAGGGACGAGCATATGTACACTGCTGCATGCCCAACCT
GGACGTTCGAGACATCATGCGGC
ACGAAGGCCAGAAAGACAGTATTGAACTATACCTTTCTAGGCTAGAGAGAGGGGGG
AAAACAGTCCCCAACTTCCAAAAG
GAAGCATTTGACAGATACGCAGAAATTCCTGAAGACGCTGTCTGTCACAATACTTTC
CAGACATGCGAACATCAGCCGAT
GCAGCAATCAGGCAGAGTGTATGCCATTGCGCTACACAGCATATATGACATACCAG
CCGATGAGTTCGGGGCGGCACTCT
TGAGGAAAAATGTCCATACGTGCTATGCCGCTTTCCACTTCTCCGAGAACCTGCTTC
TTGAAGATTCATGCGTCAATTTG
GACGAAATCAACGCGTGTTTTCGCGCGATGGAGACAAGTTGACCTTTTCTTTTGCA
TCAGAGAGTACTCTTAATTACTG
TCATAGTTATTCTAATATTCTTAAGTATGTGTGCAAAACTTACTTCCCGGCCTCTAAT
AGAGAGGTTTACATGAAGGAGT
TTTTAGTCACCAGAGTTAATACCTGGTTTTGTAAGTTTTCTAGAATAGATACTTTTCT
TTTGTACAAAGGTGTGGCCCAT
AAAAGTGTAGATAGTGAGCAGTTTTATACTGCAATGGAAGACGCATGGCATTACAA
AAAGACTCTTGCAATGTGCAACAG
CGAGAGAATCCTCCTTGAGGATTCATCATCAGTCAATTACTGGTTTCCCAAAATGAG
GGATATGGTCATCGTACCATTAT
TCGACATTTCTTTGGAGACTAGTAAGAGGACGCGCAAGGAAGTCTTAGTGTCCAAGG
ATTTCGTGTTTACAGTGCTTAAC
CACATTCGAACATACCAGGCGAAAGCTCTTACATACGCAAATGTTTTGTCCTTCGTC
GAATCGATTCGATCGAGGGTAAT
CATTAACGGTGTGACAGCGAGGTCCGAATGGGATGTGGACAAATCTTTGTTACAATC
CTTGTCCATGACGTTTTACCTGC
ATACTAAGCTTGCCGTTCTAAAGGATGACTTACTGATTAGCAAGTTTAGTCTCGGTT
CGAAAACGGTGTGCCAGCATGTG
TGGGATGAGATTTCGCTGGCGTTTGGGAACGCATTTCCCTCCGTGAAAGAGAGGCTC
TTGAACAGGAAACTTATCAGAGT
GGCAGGCGACGCATTAGAGATCAGGGTGCCTGATCTATATGTGACCTTCCACGACA
GATTAGTGACTGAGTACAAGGCCT
CTGTGGACATGCCTGCGCTTGACATTAGGAAGAAGATGGAAGAAACGGAAGTGATG
TACAATGCACTTTCAGAATTATCG

Figure 5a

```
GTGTTAAGGGAGTCTGACAAATTCGATGTTGATGTTTTTTCCCAGATGTGCCAATCTT
TGGAAGTTGACCCAATGACGGC
AGCGAAGGTTATAGTCGCGGTCATGAGCAATGAGAGCGGTCTGACTCTCACATTTGA
ACGACCTACTGAGGCGAATGTTG
CGCTAGCTTTACAGGATCAAGAGAAGGCTTCAGAAGGTGCATTGGTAGTTACCTCAA
GAGAAGTTGAAGAACCGTCCATG
AAGGGTTCGATGGCCAGAGGAGAGTTACAATTAGCTGGTCTTGCTGGAGATCATCCG
GAATCGTCCTATTCTAAGAACGA
GGAGATAGAGTCTTTAGAGCAGTTTCATATGGCGACGGCAGATTCGTTAATTCGTAA
GCAGATGAGCTCGATTGTGTACA
CGGGTCCGATTAAAGTTCAGCAAATGAAAAACTTTATCGATAGCCTGGTAGCATCAC
TATCTGCTGCGGTGTCGAATCTC
GTCAAGATCCTCAAAGATACAGCTGCTATTGACCTTGAAACCCGTCAAAAGTTTGGA
GTCTTGGATGTTGCATCTAGGAA
GTGGTTAATCAAACCAACGGCCAAGAGTCATGCATGGGGTGTTGTTGAAACCCACG
CGAGGAAGTATCATGTGGCGCTTT
TGGAATATGATGAGCAGGGTGTGGTGACATGCGATGATTGGAGAAGAGTAGCTGTT
AGCTCTGAGTCTGTTGTTTATTCC
GACATGGCGAAACTCAGAACTCTGCGCAGACTGCTTCGAAACGGAGAACCGCATGT
CAGTAGCGCAAAGGTTGTTCTTGT
GGACGGAGTTCCGGGCTGTGGAAAAACCAAAGAAATTCTTTCCAGGGTTAATTTTGA
TGAAGATCTAATTTTAGTACCTG
GGAAGCAAGCCGCGGAAATGATCAGAAGACGTGCGAATTCCTCAGGGATTATTGTG
GCCACGAAGGACAACGTTAAAACC
GTTGATTCTTTCATGATGAATTTTGGGAAAAGCACACGCTGTCAGTTCAAGAGGTTA
TTCATTGATGAAGGGTTGATGTT
GCATACTGGTTGTGTTAATTTTCTTGTGGCGATGTCATTGTGCGAAATTGCATATGTT
TACGGAGACACACAGCAGATTC
CATACATCAATAGAGTTTCAGGATTCCCGTACCCCGCCCATTTTGCCAAATTGGAAG
TTGACGAGGTGGAGACACGCAGA
ACTACTCTCCGTTGTCCAGCCGATGTCACACATTATCTGAACAGGAGATATGAGGGC
TTTGTCATGAGCACTTCTTCGGT
TAAAAAGTCTGTTTCGCAGGAGATGGTCGGCGGAGCCgCCGTGATCAATCCGATCTC
AAAACCCTTGCATGGCAAGATCT
TGACTTTTACCCAATCGGATAAAGAAGCTCTGCTTTCAAGAGGGTATTCAGATGTTC
ACACTGTGCATGAAGTGCAAGGC
GAGACATACTCTGATGTTTCACTAGTTAGGTTAACCCCTACACCGGTCTCCATCATTG
CAGGAGACAGCCCACATGTTTT
GGTCGCATTGTCAAGGCACACCTGTTCGCTCAAGTACTACACTGTTGTTATGGATCC
TTTAGTTAGTATCATTAGAGATC
TAGAGAAACTTAGCTCGTACTTGTTAGATATGTATAAGGTCGATGCAGGAACACAAT
AGCAATTACAGATTGACTCGGTG
TTCAAAGGTTCCAATCTTTTTGTTGCAGCGCCAAAGACTGGTGATATTTCTGATATGC
AGTTTTACTATGATAAGTGTCT
CCCAGGCAACAGCACCATGATGAATAATTTTGATGCTGTTACCATGAGGTTGACTGA
CATTTCATTGAATGTCAAAGATT
```

Figure 5b

```
GCATATTGGATATGTCTAAGTCTGTTGCTGCGCCTAAGGATCAAATCAAACCACTAA
TACCTATGGTACGAACGGCGGCA
GAAATGCCACGCCAGACTGGACTATTGGAAAATTTAGTGGCGATGATTAAAAGAAA
CTTTAACGCACCCGAGTTGTCTGG
CATCATTGATATTGAAAATACTGCATCTTTGGTTGTAGATAAGTTTTTTGATAGTTAT
TTGCTTAAAGAAAAAAGAAAAC
CAAATAAAAATGTTTCTTTGTTCAGTAGAGAGTCTCTCAATAGATGGTTAGAAAAGC
AGGAACAGGTAACAATAGGCCAG
CTCGCAGATTTTGATTTTGTGGATTTGCCAGCAGTTGATCAGTACAGACACATGATT
AAAGCACAACCCAAACAAAAGTT
GGACACTTCAATCCAAACGGAGTACCCGGCTTTGCAGACGATTGTGTACCATTCAAA
AAAGATCAATGCAATATTCGGCC
CGTTGTTTAGTGAGCTTACTAGGCAATTACTGGACAGTGTTGATTCGAGCAGATTTTT
GTTTTTCACAAGAAAGACACCA
GCGCAGATTGAGGATTTCTTCGGAGATCTCGACAGTCATGTGCCGATGGATGTCTTG
GAGCTGGATATATCAAAATACGA
CAAATCTCAGAATGAATTCCACTGTGCAGTAGAATACGAGATCTGGCGAAGATTGG
GTTTCGAAGACTTCTTGGGAGAAG
TTTGGAAACAAGGGCATAGAAAGACCACCCTCAAGGATTATACCGCAGGTATAAAA
ACTTGCATCTGGTATCAAAGAAAG
AGCGGGGACGTCACGACGTTCATTGGAAACACTGTGATCATTGCTGCATGTTTGGCC
TCGATGCTTCCGATGGAGAAAAT
AATCAAAGGAGCCTTTTGCGGTGACGATAGTCTGCTGTACTTTCCAAAGGGTTGTGA
GTTTCCGGATGTGCAACACTCCG
CGAATCTTATGTGGAATTTTGAAGCAAAACTGTTTAAAAAACAGTATGGATACTTTT
GCGGAAGATATGTAATACATCAC
GACAGAGGATGCATTGTGTATTACGATCCCCTAAAGTTGATCTCGAAACTTGGTGCT
AAACACATCAAGGATTGGGAACA
CTTGGAGGAGTTCAGAAGGTCTCTTTGTGATGTTGCTGTTTCGTTGAACAATTGTGCG
TATTACACACAGTTGGACGACG
CTGTATGGGAGGTTCATAAGACCGCCCCTCCAGGTTCGTTTGTTTATAAAAGTCTGG
TGAAGTATTTGTCTGATAAAGTT
CTTTTTAGAAGTTTGTTTATAGATGGCTCTAGTTGTTAAAGGAAAAGTGAATATCAA
TGAGTTTATCGACCTGACAAAAA
TGGAGAAGATCTTACCGTCGATGTTTACCCCTGTAAAGAGTGTTATGTGTTCCAAAG
TTGATAAAATAATGGTTCATGAG
AATGAGTCATTGTCAGGGGTGAACCTTCTTAAAGGAGTTAAGCTTATTGATAGTGGA
TACGTCTGTTTAGCCGGTTTGGT
CGTCACGGGCGAGTGGAACTTGCCTGACAATTGCAGAGGAGGTGTGAGCGTGTGTC
TGGTGGACAAAAGGATGGAAAGAG
CCGACGAGGCCACTCTCGGATCTTACTACACAGCAGCTGCAAAGAAAAGATTTCAG
TTCAAGGTCGTTCCCAATTATGCT
ATAACCACCCAGGACGCGATGAAAAACGTCTGGCAAGTTTTAGTTAATATTAGAAAT
GTGAAGATGTCAGCGGGTTTCTG
TCCGCTTTCTCTGGAGTTTGTGTCGGTGTGTATTGTTTATAGAAATAATATAAAATTA
GGTTTGAGAGAGAAGATTACAA
```

Figure 5c

ACGTGAGAGACGGAGGGCCCATGGAACTTACAGAAGAAGTCGTTGATGAGTTCATG
GAAGATGTCCCTATGTCGATCAGG
CTTGCAAAGTTTCGATCTCGAACCGGAAAAAGAGTGATGTCCGCAAAGGGAAAAA
TAGTAGTAGTGATCGGTCAGTGCC
GAACAAGAACTATAGAAATGTTAAGGATTTTGGAGGAATGAGTTTTAAAAAGAATA
ATTTAATCGATGATGATTCGGAGG
CTACTGTCGCCGAATCGGATTCGTTTTAAATAGATCTTACAGTATCACTACTCCATCT
CAGTTCGTGTTCTTGTCATTAA
TTAAATGGCTAGCAAAGGAGAAGAACTTTTCACTGGAGTTGTCCCAATTCTTGTTGA
ATTAGATGGTGATGTTAATGGGC
ACAAATTTTCTGTCAGTGGAGAGGGTGAAGGTGATGCTACATACGGAAAGCTTACCC
TTAAATTTATTTGCACTACTGGA
AAACTACCTGTTCCATGGCCAACACTTGTCACTACTTTCTCTTATGGTGTTCAATGCT
TTTCCCGTTATCCGGATCATAT
GAAACGGCATGACTTTTTCAAGAGTGCCATGCCCGAAGGTTATGTACAGGAACGCA
CTATATCTTTCAAAGATGACGGGA
ACTACAAGACGCGTGCTGAAGTCAAGTTTGAAGGTGATACCCTTGTTAATCGTATCG
AGTTAAAAGGTATTGATTTTAAA
GAAGATGGAAACATTCTCGGACACAAACTCGAGTACAACTATAACTCACACAATGT
ATACATCACGGCAGACAAACAAAA
GAATGGAATCAAAGCTAACTTCAAAATTCGCCACAACATTGAAGATGGATCCGTTC
AACTAGCAGACCATTATCAACAAA
ATACTCCAATTGGCGATGGCCCTGTCCTTTTACCAGACAACCATTACCTGTCGACAC
AATCTGCCCTTTCGAAAGATCCC
AACGAAAAGCGTGACCACATGGGCCTTCTTGAGTTTGTAACTGCTGCTGGGATTACA
CATGGCATGGATGAGCTCTACAA
ATAATGACACTCGAGGGGTAGTCAAGATGCATAATAAATAACGGATTGTGTCCGTA
ATCACACGTGGTGCGTACGATAAC
GCATAGTGTTTTCCCTCCACTTAAATCGAAGGGTTGTGTCTTGGATCGCGCGGGTC
AAATGTATATGGTTCATATACAT
CCGCAGGCACGTAATAAAGCGAGGGGTTCGGGTCGAGGTCGGCTGTGAAACTCGAA
AAGGTTCCGGAAAACAAAAAGAG
AGTGGTAGGTAATAGTGTTAATAATAAGAAAATAAATAATAGTGGTAAGAAAGGTT
TGAAAGTTGAGGAAATTGAGGATA
ATGTAAGTGATGACGAGTCTATCGCGTCATCGAGTACGTTTAATCAATATGCCTTA
TACAATCAACTCTCCGAGCCAAT
TTGTTTACTTAAGTTCCGCTTATGCAGATCCTGTGCAGCTGATCAATCTGTGTACAAA
TGCATTGGGTAACCAGTTTCAA
ACGCAACAAGCTAGGACAACAGTCCAACAGCAATTTGCGGATGCCTGGAAACCTGT
GCCTAGTATGACAGTGAGATTTCC
TGCATCGGATTTCTATGTGTATAGATATAATTCGACGCTTGATCCGTTGATCACGGC
GTTATTAAATAGCTTCGATACTA
GAAATAGAATAATAGAGGTTGATAATCAACCCGCACCGAATACTACTGAAATCGTT
AACGCGACTCAGAGGGTAGACGAT
GCGACTGTAGCTATAAGGGCTTCAATCAATAATTTGGCTAATGAACTGGTTCGTGGA
ACTGGCATGTTCAATCAAGCAAG

Figure 5d

CTTTGAGACTGCTAGTGGACTTGTCTGGACCACAACTCCGGCTACTTAGCTATTGTTG
TGAGATTTCCTAAAATAAAGTC
ACTGAAGACTTAAAATTCAGGGTGGCTGATACCAAAATCAGCAGTGGTTGTTCGTCC
ACTTAAATATAACGATTGTCATA
TCTGGATCCAACAGTTAAACCATGTGATGGTGTATACTGTGGTATGGCGTAAAACAA
CGGAAAAGTCGCTGAAGACTTAA
AATTCAGGGTGGCTGATACCAAAATCAGCAGTGGTTGTTCGTCCACTTAAAAATAAC
GATTGTCATATCTGGATCCAACA
GTTAAACCATGTGATGGTGTATACTGTGGTATGGCGTAAACAACGGAGAGGTTCGA
ATCCTCCCCTAACCGCGGgtagcg
gccca

Figure 5e

Complete Sequence of BSG 1057 (SEQ ID NO.: 2):

GTATTTTTACAACAATTACCAACAACAACAAACAACAGACAACATTACAATT
ACTATTTACAATTACAATGGCATACACA
CAGACAGCTACCACATCAGCTTTGCTGGACACTGTCCGAGGAAACAACTCCT
TGGTCAATGATCTAGCAAAGCGTCGTCT
TTACGACACAGCGGTTGAAGAGTTTAACGCTCGTGACCGCAGGCCCAAGGTG
AACTTTTCAAAAGTAATAAGCGAGGAGC
AGACGCTTATTGCTACCCGGGCGTATCCAGAATTCCAAATTACATTTTATAAC
ACGCAAAATGCCGTGCATTCGCTTGCA
GGTGGATTGCGATCTTTAGAACTGGAATATCTGATGATGCAAATTCCCTACGG
ATCATTGACTTATGACATAGGCGGGAA
TTTTGCATCGCATCTGTTCAAGGGACGAGCATATGTACACTGCTGCATGCCCA
ACCTGGACGTTCGAGACATCATGCGGC
ACGAAGGCCAGAAAGACAGTATTGAACTATACCTTTCTAGGCTAGAGAGAGG
GGGGAAAACAGTCCCCAACTTCCAAAAG
GAAGCATTTGACAGATACGCAGAAATTCCTGAAGACGCTGTCTGTCACAATA
CTTTCCAGACATGCGAACATCAGCCGAT
GCAGCAATCAGGCAGAGTGTATGCCATTGCGCTACACAGCATATATGACATA
CCAGCCGATGAGTTCGGGGCGGCACTCT
TGAGGAAAAATGTCCATACGTGCTATGCCGCTTTCCACTTCTCCGAGAACCTG
CTTCTTGAAGATTCATGCGTCAATTTG
GACGAAATCAACGCGTGTTTTCGCGCGATGGAGACAAGTTGACCTTTTCTTT
TGCATCAGAGAGTACTCTTAATTACTG
TCATAGTTATTCTAATATTCTTAAGTATGTGTGCAAAACTTACTTCCCGGCCTC
TAATAGAGAGGTTTACATGAAGGAGT
TTTTAGTCACCAGAGTTAATACCTGGTTTTGTAAGTTTTCTAGAATAGATACTT
TTCTTTTGTACAAAGGTGTGGCCCAT
AAAAGTGTAGATAGTGAGCAGTTTTATACTGCAATGGAAGACGCATGGCATT
ACAAAAAGACTCTTGCAATGTGCAACAG
CGAGAGAATCCTCCTTGGGGATTCATCATCAGTCAATTACTGGTTTCCCAAAA
TGAGGGATATGGTCATCGTACCATTAT
TCGACATTTCTTTGGAGACTAGTAAGAGGACGCGCAAGGAAGTCTTAGTGTC
CAAGGATTTCGTGTTCACAGTGCTTAAC
CACATTCGAACATACCAGGCGAAAGCTCTTACATACGCAAATGTTTTGTCCTT
CGTCGAATCGATTCGATCGAGGGTAAT
CATTAACGGTGTGACAGCGAGGTCCGAATGGGATGTGGACAAATCTTTGTTA
CAATCCTTGTCCATGACGTTTTACCTGC
ATACTAAGCTTGCCGTTCTAAAGGATGACTTACTGATTAGCAAGTTTAGTCTC
GGTTCGAAAACGGTGTGCCAGCATGTG
TGGGATGAGATTTCGCTGGCGTTTGGGAACGCATTTCCCTCCGTGAAAGAGA
GGCTCTTGAACAGGAAACTTATCAGAGT
GGCAGGCGACGCATTAGAGATCAGGGTGCCTGATCTATATGTGACCTTCCAC
GACAGATTAGTGACTGAGTACAAGGCCT
CTGTGGACATGCCTGCGCTTGACATTAGGAAGAAGATGGAAGAAACGGAAGT
GATGTACAATGCACTTTCAGAATTATCG

Figure 6a

```
GTGTTAAGGGAGTCTGACAAATTCGATGTTGATGTTTTTCCCAGATGTGCCA
ATCTTTGGAAGTTGACCCAATGACGGC
AGCGAAGGTTATAGTCGCGGTCATGAGCAATGAGAGCGGTCTGACTCTCACA
TTTGAACGACCTACTGAGGCGAATGTTG
CGCTAGCTTTACAGGATCAAGAGAAGGCTTCAGAAGGTGCATTGGTAGTTAC
CTCAAGAGAAGTTGAAGAACCGTCCATG
AAGGGTTCGATGGCCAGAGGAGAGTTACAATTAGCTGGTCTTGCTGGAGATC
ATCCGGAATCGTCCTATTCTAAGAACGA
GGAGATAGAGTCTTTAGAGCAGTTTCATATGGCGACGGCAGATTCGTTAATTC
GTAAGCAGATGAGCTCGATTGTGTACA
CGGGTCCGATTAAAGTTCAGCAAATGAAAAACTTTATCGATAGCCTGGTAGC
ATCACTATCTGCTGCGGTGTCGAATCTC
GTCAAGATCCTCAAAGATACAGCTGCTATTGACCTTGAAACCCGTCAAAAGT
TTGGAGTCTTGGATGTTGCATCTAGGAA
GTGGTTAATCAAACCAACGGCCAAGAGTCATGCATGGGGTGTTGTTGAAACC
CACGCGAGGGAGTATCATGTGGCGCTTT
TGGAATATGATGAGCAGGGTGTGGTGACATGCGATGATTGGAGAAGAGTAGC
TGTTAGCTCTGAGTCTGTTGTTTATTCC
GACATGGCGAAACTCAGAACTCTGCGCAGACTGCTTCGAAACGGAGAACCGC
ATGTCAGTAGCGCAAAGGTTGTTCTTGT
GGACGGAGTTCCGGGCTGTGGAAAAACCAAAGAAATTCTTTCCAGGGTTAAT
TTTGATGAAGATCTAATTTTAGTACCTG
GGAAGCAAGCCGCGGAAATGATCAGAAGACGTGCGAATTCCTCAGGGATTAT
TGTGGCCACGAAGGACAACGTTAAAACC
GTTGATTCTTTCATGATGAATTTTGGGAAAAGCACACGCTGTCAGTTCAAGAG
GTTATTCATTGATGAAGGGTTGATGTT
GCATACTGGTTGTGTTAATTTTCTTGTGGCGATGTCATTGTGCGAAATTGCAT
ATGTTTACGGAGACACACAGCAGATTC
CATACATCAATAGAGTTTCAGGATTCCCGTACCCCGCCCATTTTGCCAAATTG
GAAGTTGACGAGGTGGAGACACGCAGA
ACTACTCTCCGTTGTCCAGCCGATGTCACACATTATCTGAACAGGAGATATGA
GGGCTTTGTCATGAGCACTTCTTCGGT
TAAAAAGTCTGTTTCGCAGGAGATGGTCGGCGGAGCCGCCGTGATCAATCCG
ATCTCAAAACCCTTGCATGGCAAGATCC
TGACTTTTACCCAATCGGATAAAGAAGCTCTGCTTTCAAGAGGGTATTCAGAT
GTTCACACTGTGCATGAAGTGCAAGGC
GAGACATACTCTGATGTTTCACTAGTTAGGTTAACCCCTACACCGGTCTCCAT
CATTGCAGGAGACAGCCCACATGTTTT
GGTCGCATTGTCAAGGCACACCTGTTCGCTCAAGTACTACACTGTTGTTATGG
ATCCTTTAGTTAGTATCATTAGAGATC
TAGAGAAACTTAGCTCGTACTTGTTAGATATGTATAAGGTCGATGCAGGAAC
ACAATAGCAATTACAGATTGACTCGGTG
TTCAAAGGTTCCAATCTTTTGTTGCAGCGCCAAAGACTGGTGATATTTCTGA
TATGCAGTTTTACTATGATAAGTGTCT
CCCAGGCAACAGCACCATGATGAATAATTTTGATGCTGTTACCATGAGGTTG
ACTGACATTTCATTGAATGTCAAAGATT
```

Figure 6b

GCATATTGGATATGTCTAAGTCTGTTGCTGCACCTAAGGATCAAATCAAACCA
CTAATACCTATGGTACGAACGGCGGCA
GAAATGCCACGCCAGACTGGACTATTGGAAAATTTAGTGGCGATGATTAAAA
GAAACTTTAACGCACCCGAGTTGTCTGG
CATCATTGATATTGAAAATACTGCATCTTTGGTTGTAGATAAGTTTTTTGATA
GTTATTTGCTTAAAGAAAAAAGAAAAC
CAAATAAAAATGTTTCTTTGTTCAGTAGAGAGTCTCTCAATAGATGGTTAGAA
AAGCAGGAACAGGTAACAATAGGCCAG
CTCGCAGATTTTGATTTTGTGGATTTGCCAGCAGTTGATCAGTACAGACACAT
GATTAAAGCACAACCCAAACAAAAGTT
GGACACTTCAATCCAAACGGAGTACCCGGCTTTGCAGACGATTGTGTACCAT
TCAAAAAGATCAATGCAATATTCGGCC
CGTTGTTTAGTGAGCTTACTAGGCAATTACTGGACAGTGTTGATTCGAGCAGA
TTTTTGTTTTTCACAAGAAAGACACCA
GCGCAGATTGAGGATTTCTTCGGAGATCTCGACAGTCATGTGCCGATGGATG
TCTTGGAGCTGGATATATCAAAATACGA
CAAATCTCAGAATGAATTCCACTGTGCAGTAGAATACGAGATCTGGCGAAGA
TTGGGTTTCGAAGACTTCTTGGGAGAAG
TTTGGAAACAAGGGCATAGAAAGACCACCCTCAAGGATTATACCGCAGGTAT
AAAAACTTGCATCTGGTATCAAAGAAAG
AGCGGGGACGTCACGACGTTCATTGGAAACACTGTGATCATTGCTGCATGTTT
GGCCTCGATGCTTCCGATGGAGAAAAT
AATCAAAGGAGCCTTTTGCGGTGACGATAGTCTGCTGTACTTTCCAAAGGGTT
GTGAGTTTCCGGATGTGCAACACTCCG
CGAATCTTATGTGGAATTTTGAAGCAAAACTGTTTAAAAAACAGTATGGATA
CTTTTGCGGAAGATATGTAATACATCAC
GACAGAGGATGCATTGTGTATTACGATCCCCTAAAGTTGATCTCGAAACTTG
GTGCTAAACACATCAAGGATTGGGAACA
CTTGGAGGAGTTCAGAAGGTCTCTTTGTGATGTTGCTGTTTCGTTGAACAATT
GTGCGTATTACACACAGTTGGACGACG
CTGTATGGGAGGTTCATAAGACCGCCCCTCCAGGTTCGTTTGTTTATAAAAGT
CTGGTGAAGTATTTGTCTGATAAAGTT
CTTTTTAGAAGTTTGTTTATAGATGGCTCTAGTTGTTAAAGGAAAAGTGAATA
TCAATGAGTTTATCGACCTGACAAAAA
TGGAGAAGATCTTACCGTCGATGTTTACCCCTGTAAAGAGTGTTATGTGTTCC
AAAGTTGATAAAATAATGGTTCATGAG
AATGAGTCATTGTCAGGGGTGAACCTTCTTAAAGGAGTTAAGCTTATTGATAG
TGGATACGTCTGTTTAGCCGGTTTGGT
CGTCACGGGCGAGTGGAACTTGCCTGACAATTGCAGAGGAGGTGTGAGCGTG
TGTCTGGTGGACAAAAGGATGGAAAGAG
CCGACGAGGCCATTCTCGGATCTTACTACACAGCAGCTGCAAAGAAAAGATT
TCAGTTCAAGGTCGTTCCCAATTATGCT
ATAACCACCCAGGACGCGATGAGAAACGTCTGGCAAGTTTTAGTTAATATTA
GAAATGTGAAGATGTCAGCGGGTTTCTG
TCCGCTTTCTCTGGAGTTTGTGTCGGTGTGTATTGTTTATAGAAATAATATAA
AATTAGGTTTGAGAGAGAAGATTACAA

Figure 6c

ACGTGAGAGACGGAGGGCCCATGGAACTTACAGAAGAAGTCGTTGATGAGTT
CATGGAAGATGTCCCTATGTCGATCAGG
CTTGCAAAGTTTCGATCTCGAACCGGAAAAAAGAGTGATGTCCGCAAAGGGA
AAAATAGTAGTAGTGATCGGTCAGTGCC
GAACAAGAACTATAGAAATGTTAAGGATTTTGGAGGAATGAGTTTTAAAAAG
AATAATTTAATCGATGATGATTCGGAGG
CTACTGTCGCCGAATCGGATTCGTTTTAAATAGATCTTACAGTATCACTACTC
CATCTCAGTTCGTGTTCTTGTCAttaa
ttaaATGGCTAGCAAAGGAGAAGAACTTTTCACTGGAGTTGTCCCAATTCTTGTT
GAATTAGATGGTGATGTTAATGGGC
ACAAATTTTCTGTCAGTGGAGAGGGTGAAGGTGATGCTACATACGGAAAGCT
TACACTTAAATTTATTTGCACTACTGGA
AAACTACCTGTTCCATGGCCAACACTTGTCACTACTTTCTCTTATGGTGTTCA
ATGCTTTTCCCGTTATCCGGATCATAT
GAAACGGCATGACTTTTTCAAGAGTGCCATGCCCGAAGGTTATGTACAGGAA
CGCACTATATCTTTCAAAGATGACGGGA
ACTACAAGACGCGTGCTGAAGTCAAGTTTGAAGGTGATACCCTTGTTAATCG
TATCGAGTTAAAAGGTATTGATTTTAAA
GAAGATGGAAACATTCTCGGACACAAACTCGAGTACAACTATAACTCACACA
ATGTATACATCACGGCAGACAAACAAAA
GAATGGAATCAAAGCTAACTTCAAAATTCGCCACAACATTGAAGATGGATCC
GTTCAACTAGCAGACCATTATCAACAAA
ATACTCCAATTGGCGATGGCCCTGTCCTTTTACCAGACAACCATTACCTGTCG
ACACAATCTGCCCTTTCGAAAGATCCC
AACGAAAAGCGTGACCACATGGTCCTTCTTGAGTTTGTAACTGCTGCTGGGAT
TACACATGGCATGGATGAGCTCTACAA
ATAATGACACTCGAGGGGTAGTCAAGATGCATAATAAATAACGGATTGTGTC
CGTAATCACACGTGGTGCGTACGATAAC
GCATAGTGTTTTCCCTCCACTTAAATCGAAGGGTTGTGTCTTGGATCGCGCG
GGTCAAATGTATATGGTTCATATACAT
CCGCAGGCACGTAATAAAGCGAGGGGTTCGGGTCGAGGTCGGCTGTGAAACT
CGAAAAGGTTCCGGAAAACAAAAAAGAG
AGTGGTAGGTAATAGTGTTAATAATAAGAAAATAAATAATAGTGGTAAGAAA
GGTTTGAAAGTTGAGGAAATTGAGGATA
ATGTAAGTGATGACGAGTCTATCGCGTCATCGAGTACGTTTTAATCAATATGC
CTTATACAATCAACTCTCCGAGCCAAT
TTGTTTACTTAAGTTCCGCTTATGCAGATCCTGTGCAGCTGATCAATCTGTGT
ACAAATGCATTGGGTAACCAGTTTCAA
ACGCAACAAGCTAGGACAACAGTCCAACAGCAATTTGCGGATGCCTGGAAAC
CTGTGCCTAGTATGACAGTGAGATTTCC
TGCATCGGATTTCTATGTGTATAGATATAATTCGACGCTTGATCCGTTGATCA
CGGCGTTATTAAATAGCTTCGATACTA
GAAATAGAATAATAGAGGTTGATAATCAACCCGCACCGAATACTACTGAAAT
CGTTAACGCGACTCAGAGGGTAGACGAT
GCGACTGTAGCTATAAGGGCTTCAATCAATAATTTGGCTAATGAACtGGTTCG
TGGAACTGGCaTGTTCAATCAAGCAAG

Figure 6d

CTTTGAGACTGCTAGTGGACTTGTCTGGACCACAACTCCGGCTACTTAGctattgtt
gtgagatttcctaaaataaagtc
actgaagacttaaaattcagggtggctgataccaaaatcagcagtggttgttcgtccacttaaatataacgattgtcata
tctggatccaacagttaaaccatgtgatggtgtatactgtggtatggcgtaaaacaacggaaaagtcgctgaagacttaa
aattcagggtggctgataccaaaatcagcagtggttgttcgtccacttaaaaataacgattgtcatatctggatccaaca
gttaaaccatgtgatggtgtatactgtggtatggcgtaaaacaacggagaggttcgaatcctcccctaaccgcgggtagc
ggccca

Figure 6e

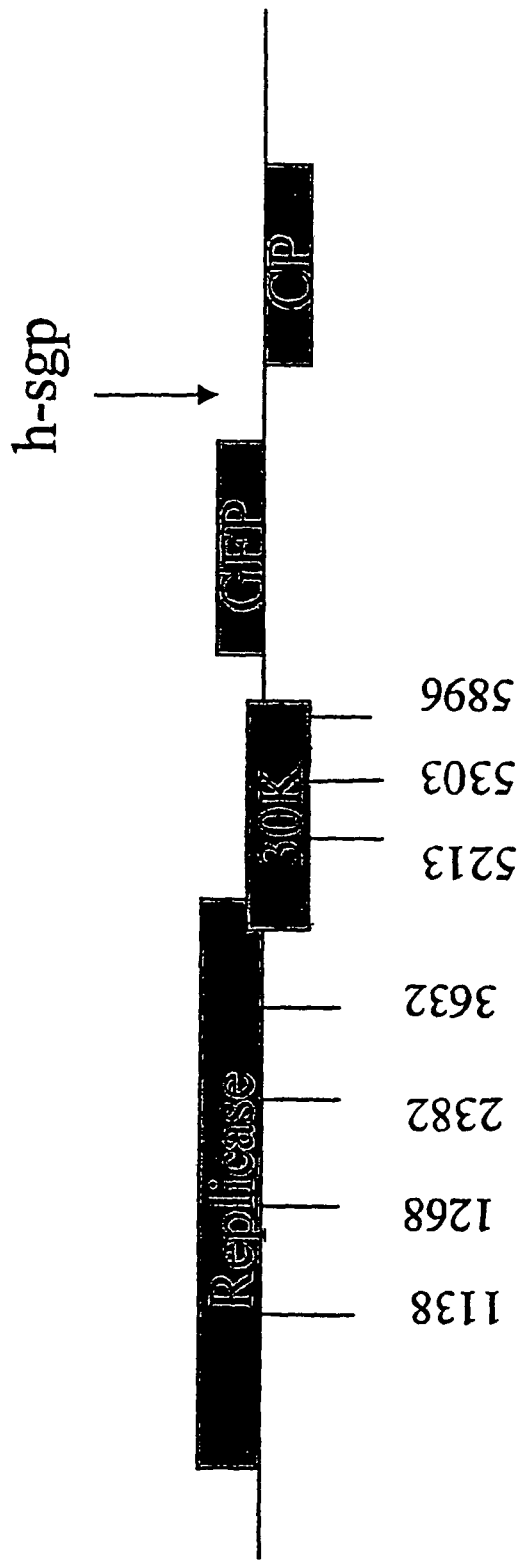
Schematic map of location of mutations in BSG 1057. 30K = movement protein; GFP = green fluorescent protein; CP = coat protein. Nucleotide positions of BSG 1057 mutations are noted.
Figur 7

SEQUENCE LISTING

```
<160> NUMBER OF SEQ ID NOS: 6

<210> SEQ ID NO 1
<211> LENGTH: 7685
<212> TYPE: DNA
<213> ORGANISM: Nicotiana tabacum

<400> SEQUENCE: 1
gtatttttac aacaattacc aacaacaaca aacaacagac aacattacaa ttactattta      60
caattacaat ggcatacaca cagacagcta ccacatcagc tttgctggac actgtccgag     120
gaaacaactc cttggtcaat gatctagcaa agcgtcgtct ttacgacaca gcggttgaag     180
agtttaacgc tcgtgaccgc aggcccaagg tgaacttttc aaaagtaata agcgaggagc     240
agacgcttat tgctacccgg gcgtatccag aattccaaat tacattttat aacacgcaaa     300
atgccgtgca ttcgcttgca ggtggattgc gatctttaga actggaatat ctgatgatgc     360
aaattcccta cggatcattg acttatgaca taggcgggaa ttttgcatcg catctgttca     420
agggacgagc atatgtacac tgctgcatgc ccaacctgga cgttcgagac atcatgcggc     480
```

-continued

| | |
|---|---|
| acgaaggcca gaaagacagt attgaactat acctttctag gctagagaga ggggggaaaa | 540 |
| cagtccccaa cttccaaaag gaagcatttg acagatacgc agaaattcct gaagacgctg | 600 |
| tctgtcacaa tactttccag acatgcgaac atcagccgat gcagcaatca ggcagagtgt | 660 |
| atgccattgc gctacacagc atatatgaca taccagccga tgagttcggg gcggcactct | 720 |
| tgaggaaaaa tgtccatacg tgctatgccg ctttccactt ctccgagaac ctgcttcttg | 780 |
| aagattcatg cgtcaatttg gacgaaatca acgcgtgttt tcgcgcgat ggagacaagt | 840 |
| tgacctttc ttttgcatca gagagtactc ttaattactg tcatagttat tctaatattc | 900 |
| ttaagtatgt gtgcaaaact tacttcccgg cctctaatag agaggtttac atgaaggagt | 960 |
| ttttagtcac cagagttaat acctggtttt gtaagttttc tagaatagat acttttcttt | 1020 |
| tgtacaaagg tgtggcccat aaaagtgtag atagtgagca gttttatact gcaatggaag | 1080 |
| acgcatggca ttacaaaaag actcttgcaa tgtgcaacag cgagagaatc ctccttgagg | 1140 |
| attcatcatc agtcaattac tggtttccca aatgaggga tatggtcatc gtaccattat | 1200 |
| tcgacatttc tttggagact agtaagagga cgcgcaagga agtcttagtg tccaaggatt | 1260 |
| tcgtgtttac agtgcttaac cacattcgaa cataccaggc gaaagctctt acatacgcaa | 1320 |
| atgttttgtc cttcgtcgaa tcgattcgat cgagggtaat cattaacggt gtgacagcga | 1380 |
| ggtccgaatg ggatgtggac aaatctttgt tacaatcctt gtccatgacg ttttacctgc | 1440 |
| atactaagct tgccgttcta aaggatgact tactgattag caagtttagt ctcggttcga | 1500 |
| aaacggtgtg ccagcatgtg tgggatgaga tttcgctggc gtttgggaac gcatttccct | 1560 |
| ccgtgaaaga gaggctcttg aacaggaaac ttatcagagt ggcaggcgac gcattagaga | 1620 |
| tcagggtgcc tgatctatat gtgaccttcc acgacagatt agtgactgag tacaaggcct | 1680 |
| ctgtggacat gcctgcgctt gacattagga agaagatgga agaaacggaa gtgatgtaca | 1740 |
| atgcactttc agaattatcg gtgttaaggg agtctgacaa attcgatgtt gatgtttttt | 1800 |
| cccagatgtg ccaatctttg gaagttgacc caatgacggc agcgaaggtt atagtcgcgg | 1860 |
| tcatgagcaa tgagagcggt ctgactctca catttgaacg acctactgag gcgaatgttg | 1920 |
| cgctagcttt acaggatcaa gagaaggctt cagaaggtgc attggtagtt acctcaagag | 1980 |
| aagttgaaga accgtccatg aagggttcga tggccagagg agagttacaa ttagctggtc | 2040 |
| ttgctggaga tcatccggaa tcgtcctatt ctaagaacga ggagatagag tctttagagc | 2100 |
| agtttcatat ggcgacggca gattcgttaa ttcgtaagca gatgagctcg attgtgtaca | 2160 |
| cgggtccgat taaagttcag caaatgaaaa actttatcga tagcctggta gcatcactat | 2220 |
| ctgctgcgt gtcgaatctc gtcaagatcc tcaaagatac agctgctatt gaccttgaaa | 2280 |
| cccgtcaaaa gtttggagtc ttggatgttg catctaggaa gtggttaatc aaaccaacgg | 2340 |
| ccaagagtca tgcatggggt gttgttgaaa cccacgcgag gaagtatcat gtggcgcttt | 2400 |
| tggaatatga tgagcagggt gtggtgacat gcgatgattg gagaagagta gctgttagct | 2460 |
| ctgagtctgt tgtttattcc gacatggcga aactcagaac tctgcgcaga ctgcttcgaa | 2520 |
| acggagaacc gcatgtcagt agcgcaaagg ttgttcttgt ggacggagtt ccgggctgtg | 2580 |
| gaaaaaccaa agaaattctt tccagggtta attttgatga agatctaatt ttagtacctg | 2640 |
| ggaagcaagc cgcggaaatg atcagaagac gtgcgaattc ctcagggatt attgtggcca | 2700 |
| cgaaggacaa cgttaaaacc gttgattctt tcatgatgaa ttttgggaaa agcacacgct | 2760 |
| gtcagttcaa gaggttattc attgatgaag ggttgatgtt gcatactggt tgtgttaatt | 2820 |
| ttcttgtggc gatgtcattg tgcgaaattg catatgttta cggagacaca cagcagattc | 2880 |

-continued

```
catacatcaa tagagtttca ggattcccgt accccgccca ttttgccaaa ttggaagttg    2940
acgaggtgga gacacgcaga actactctcc gttgtccagc cgatgtcaca cattatctga    3000
acaggagata tgagggcttt gtcatgagca cttcttcggt taaaaagtct gtttcgcagg    3060
agatggtcgg cggagccgcc gtgatcaatc cgatctcaaa accccttgcat ggcaagatct    3120 tgactttttac ccaatcggat aaagaagctc tgctttcaag agggtattca gatgttcaca    3180
ctgtgcatga agtgcaaggc gagacatact ctgatgtttc actagttagg ttaacccta    3240 caccggtctc catcattgca ggagacagcc cacatgtttt ggtcgcattg tcaaggcaca    3300
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt tgttgcagcg ccaaagactg    3480
gtgatatttc tgatatgcag ttttactatg ataagtgtct cccaggcaac agcaccatga    3540
tgaataattt tgatgctgtt accatgaggt tgactgacat ttcattgaat gtcaaagatt    3600
gcatattgga tatgtctaag tctgttgctg cgcctaagga tcaaatcaaa ccactaatac    3660
ctatggtacg aacggcggca gaaatgccac gccagactgg actattggaa aatttagtgg    3720
cgatgattaa aagaaacttt aacgcacccg agttgtctgg catcattgat attgaaaata    3780
ctgcatcttt ggttgtagat aagttttttg atagttattt gcttaaagaa aaagaaaac    3840 caaataaaaa tgtttctttg ttcagtagag agtctctcaa tagatggtta gaaaagcagg    3900
aacaggtaac aataggccag ctcgcagatt ttgattttgt ggatttgcca gcagttgatc    3960
agtacagaca catgattaaa gcacaaccca acaaaagtt ggacacttca atccaaacgg    4020
agtacccggc tttgcagacg attgtgtacc attcaaaaaa gatcaatgca atattcggcc    4080
cgttgtttag tgagcttact aggcaattac tggacagtgt tgattcgagc agattttttgt    4140 ttttcacaag aaagacacca gcgcagattg aggatttctt cggagatctc gacagtcatg    4200
tgccgatgga tgtcttggag ctggatatat caaaatacga caaatctcag aatgaattcc    4260
actgtgcagt agaatacgag atctggcgaa gattgggttt cgaagacttc ttgggagaag    4320
tttggaaaca agggcataga aagaccaccc tcaaggatta taccgcaggt ataaaaactt    4380
gcatctggta tcaaagaaag agcggggacg tcacgacgtt cattggaaac actgtgatca    4440
ttgctgcatg tttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga acttttgcg    4620 gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgccctc caggttcgtt tgtttataaa agtctggtga    4860
agtatttgtc tgataaagtt cttttttagaa gtttgtttat agatggctct agttgttaaa    4920
ggaaaagtga atatcaatga gtttatcgac ctgacaaaaa tggagaagat cttaccgtcg    4980
atgtttaccc ctgtaaagag tgttatgtgt tccaaagttg ataaataat ggttcatgag    5040 aatgagtcat tgtcagggt gaaccttctt aaaggagtta agcttattga tagtggatac    5100
gtctgtttag ccggttttggt cgtcacgggc gagtggaact tgcctgacaa ttgcagagga    5160
ggtgtgagcg tgtgtctggt ggacaaaagg atggaaagag ccgacgaggc cactctcgga    5220
```

-continued

```
tcttactaca cagcagctgc aaagaaaaga tttcagttca aggtcgttcc caattatgct    5280
ataaccaccc aggacgcgat gaaaaacgtc tggcaagttt tagttaatat tagaaatgtg    5340
aagatgtcag cgggtttctg tccgctttct ctggagtttg tgtcggtgtg tattgtttat    5400
agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa agagtgatg tccgcaaagg gaaaaatagt    5580
agtagtgatc ggtcagtgcc gaacaagaac tatagaaatg ttaaggattt tggaggaatg    5640
agttttaaaa agaataattt aatcgatgat gattcggagg ctactgtcgc cgaatcggat    5700
tcgttttaaa tagatcttac agtatcacta ctccatctca gttcgtgttc ttgtcattaa    5760
ttaaatggct agcaaaggag aagaactttt cactggagtt gtcccaattc ttgttgaatt    5820
agatggtgat gttaatgggc acaaattttc tgtcagtgga gagggtgaag gtgatgctac    5880
atacggaaag cttaccctta aatttatttg cactactgga aaactacctg ttccatggcc    5940
aacacttgtc actactttct cttatggtgt tcaatgcttt tcccgttatc cggatcatat    6000
gaaacggcat gacttttca agagtgccat gcccgaaggt tatgtacagg aacgcactat    6060
atctttcaaa gatgacggga actacaagac gcgtgctgaa gtcaagtttg aaggtgatac    6120
ccttgttaat cgtatcgagt taaaggtat tgattttaaa gaagatggaa acattctcgg    6180
acacaaactc gagtacaact ataactcaca caatgtatac atcacggcag acaaacaaaa    6240
gaatggaatc aaagctaact tcaaaattcg ccacaacatt gaagatggat ccgttcaact    6300
agcagaccat tatcaacaaa atactccaat tggcgatggc cctgtccttt taccagacaa    6360
ccattacctg tcgacacaat ctgccctttc gaaagatccc aacgaaaagc gtgaccacat    6420
gggccttctt gagtttgtaa ctgctgctgg gattacacat ggcatggatg agctctacaa    6480
ataatgacac tcgagggta gtcaagatgc ataataaata acggattgtg tccgtaatca    6540
cacgtggtgc gtacgataac gcatagtgtt tttccctcca cttaaatcga agggttgtgt    6600
cttggatcgc gcgggtcaaa tgtatatggt tcatatacat ccgcaggcac gtaataaagc    6660
gagggggttcg ggtcgaggtc ggctgtgaaa ctcgaaaagg ttccggaaaa caaaaaagag    6720
agtggtaggt aatagtgtta ataataagaa aataaataat agtggtaaga aaggtttgaa    6780
agttgaggaa attgaggata atgtaagtga tgacgagtct atcgcgtcat cgagtacgtt    6840
ttaatcaata tgccttatac aatcaactct ccgagccaat tgttttactt aagttccgct    6900
tatgcagatc ctgtgcagct gatcaatctg tgtacaaatg cattgggtaa ccagtttcaa    6960
acgcaacaag ctaggacaac agtccaacag caatttgcgg atgcctggaa acctgtgcct    7020
agtatgacag tgagatttcc tgcatcggat ttctatgtgt atagatataa ttcgacgctt    7080
gatccgttga tcacggcgtt attaaatagc ttcgatacta gaaatagaat aatagaggtt    7140
gataatcaac ccgcaccgaa tactactgaa atcgttaacg cgactcagag ggtagacgat    7200
gcgactgtag ctataagggc ttcaatcaat aatttggcta atgaactggt tcgtggaact    7260
ggcatgttca atcaagcaag ctttgagact gctagtggac ttgtctggac cacaactccg    7320
gctacttagc tattgttgtg agatttccta aaataaagtc actgaagact taaaattcag    7380
ggtggctgat accaaaatca gcagtggttg ttcgtccact taaatataac gattgtcata    7440
tctggatcca acagttaaac catgtgatgg tgtatactgt ggtatggcgt aaaacaacgg    7500
aaaagtcgct gaagacttaa aattcagggt ggctgatacc aaaatcagca gtggttgttc    7560
gtccacttaa aaataacgat tgtcatatct ggatccaaca gttaaaccat gtgatggtgt    7620
```

```
atactgtggt atggcgtaaa caacggagag gttcgaatcc tcccctaacc gcgggtagcg    7680
gccca                                                                7685

<210> SEQ ID NO 2
<211> LENGTH: 7686
<212> TYPE: DNA
<213> ORGANISM: Nicotiana tabacum

<400> SEQUENCE: 2 gtattttac  aacaattacc  aacaacaaca  acaacagac   aacattacaa ttactattta     60
caattacaat ggcatacaca cagacagcta ccacatcagc tttgctggac actgtccgag       120
gaaacaactc cttggtcaat gatctagcaa agcgtcgtct ttacgacaca gcggttgaag       180
agtttaacgc tcgtgaccgc aggcccaagg tgaactttc  aaaagtaata agcgaggagc      240
agacgcttat tgctacccgg gcgtatccag aattccaaat tacatttat  aacacgcaaa      300 atgccgtgca ttcgcttgca ggtggattgc gatctttaga actggaatat ctgatgatgc      360
aaattcccta cggatcattg acttatgaca taggcgggaa ttttgcatcg catctgttca      420
agggacgagc atatgtacac tgctgcatgc ccaacctgga cgttcgagac atcatgcggc      480
acgaaggcca gaaagacagt attgaactat acctttctag gctagagaga ggggggaaaa      540
cagtccccaa cttccaaaag gaagcatttg acagatacgc agaaattcct gaagacgctg      600
tctgtcacaa tactttccag acatgcgaac atcagccgat gcagcaatca ggcagagtgt      660
atgccattgc gctacacagc atatatgaca taccagccga tgagttcggg gcggcactct      720
tgaggaaaaa tgtccatacg tgctatgccg ctttccactt ctccgagaac ctgcttcttg      780
aagattcatg cgtcaatttg gacgaaatca acgcgtgttt ttcgcgcgat ggagacaagt      840
tgaccttttc ttttgcatca gagagtactc ttaattactg tcatagttat tctaatattc      900
ttaagtatgt gtgcaaaact tacttcccgg cctctaatag agaggtttac atgaaggagt      960
ttttagtcac cagagttaat acctggtttt gtaagttttc tagaatagat acttttcttt     1020
tgtacaaagg tgtggcccat aaaagtgtag atagtgagca gttttatact gcaatggaag     1080
acgcatggca ttacaaaaag actcttgcaa tgtgcaacag cgagagaatc ctccttgggg     1140
attcatcatc agtcaattac tggttttccca aaatgaggga tatggtcatc gtaccattat     1200
tcgacatttc tttggagact agtaagagga cgcgcaagga agtcttagtg tccaaggatt     1260
tcgtgttcac agtgcttaac cacattcgaa cataccaggc gaaagctctt acatacgcaa     1320
atgttttgtc cttcgtcgaa tcgattcgat cgagggtaat cattaacggt gtgacagcga     1380
ggtccgaatg ggatgtggac aaatctttgt tacaatcctt gtccatgacg ttttacctgc     1440
atactaagct tgccgttcta aaggatgact tactgattag caagtttagt ctcggttcga     1500
aaacggtgtg ccagcatgtg tgggatgaga tttcgctggc gtttgggaac gcatttccct     1560
ccgtgaaaga gaggctcttg aacaggaaac ttatcagagt ggcaggcgac gcattagaga     1620
tcagggtgcc tgatctatat gtgaccttcc acgacagatt agtgactgag tacaaggcct     1680
ctgtggacat gcctgcgctt gacattagga agaagatgga agaaacggaa gtgatgtaca     1740
atgcactttc agaattatcg gtgttaaggg agtctgacaa attcgatgtt gatgtttttt     1800
cccagatgtg ccaatctttg gaagttgacc caatgacggc agcgaaggtt atagtcgcgg     1860
tcatgagcaa tgagagcggt ctgactctca catttgaacg acctactgag gcgaatgttg     1920
cgctagcttt acaggatcaa gagaaggctt cagaaggtgc attggtagtt acctcaagag     1980
```

```
aagttgaaga accgtccatg aagggttcga tggccagagg agagttacaa ttagctggtc    2040
ttgctggaga tcatccggaa tcgtcctatt ctaagaacga ggagatagag tctttagagc    2100
agtttcatat ggcgacggca gattcgttaa ttcgtaagca gatgagctcg attgtgtaca    2160
cgggtccgat taaagttcag caaatgaaaa actttatcga tagcctggta gcatcactat    2220
ctgctgcggt gtcgaatctc gtcaagatcc tcaaagatac agctgctatt gaccttgaaa    2280
cccgtcaaaa gtttggagtc ttggatgttg catctaggaa gtggttaatc aaaccaacgg    2340
ccaagagtca tgcatgggt gttgttgaaa cccacgcgag ggagtatcat gtggcgcttt     2400
tggaatatga tgagcagggt gtggtgacat gcgatgattg gagaagagta gctgttagct    2460
ctgagtctgt tgtttattcc gacatggcga aactcagaac tctgcgcaga ctgcttcgaa    2520
acggagaacc gcatgtcagt agcgcaaagg ttgttcttgt ggacggagtt ccgggctgtg    2580
gaaaaaccaa agaaattctt tccagggtta attttgatga agatctaatt ttagtacctg    2640
ggaagcaagc cgcggaaatg atcagaagac gtgcgaattc ctcagggatt attgtggcca    2700
cgaaggacaa cgttaaaacc gttgattctt tcatgatgaa ttttgggaaa agcacacgct    2760
gtcagttcaa gaggttattc attgatgaag ggttgatgtt gcatactggt tgtgttaatt    2820
ttcttgtggc gatgtcattg tgcgaaattg catatgttta cggagacaca cagcagattc    2880
catacatcaa tagagtttca ggattcccgt accccgccca ttttgccaaa ttggaagttg    2940
acgaggtgga gacacgcaga actactctcc gttgtccagc cgatgtcaca cattatctga    3000
acaggagata tgagggcttt gtcatgagca cttcttcggt taaaaagtct gtttcgcagg    3060
agatggtcgg cggagccgcc gtgatcaatc cgatctcaaa accttgcat ggcaagatcc     3120 tgactttac ccaatcggat aaagaagctc tgctttcaag agggtattca gatgttcaca     3180
ctgtgcatga agtgcaaggc gagacatact ctgatgtttc actagttagg ttaaccccta    3240
caccggtctc catcattgca ggagacagcc cacatgtttt ggtcgcattg tcaaggcaca    3300
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt tgttgcagcg ccaaagactg    3480
gtgatatttc tgtatatgcag ttttactatg ataagtgtct cccaggcaac agcaccatga   3540
tgaataattt tgatgctgtt accatgaggt tgactgacat ttcattgaat gtcaaagatt    3600
gcatattgga tatgtctaag tctgttgctg cacctaagga tcaaatcaaa ccactaatac    3660
ctatggtacg aacggcggca gaaatgccac gccagactgg actattggaa aatttagtgg    3720
cgatgattaa aagaaacttt aacgcacccg agttgtctgg catcattgat attgaaaata    3780
ctgcatcttt ggttgtagat aagtttttg atagttattt gcttaaagaa aaagaaaac     3840 caaataaaaa tgtttctttg ttcagtagag agtctctcaa tagatggtta gaaaagcagg    3900
aacaggtaac aataggccag ctcgcagatt ttgattttgt ggatttgcca gcagttgatc    3960
agtacagaca catgattaaa gcacaaccca acaaaagtt ggacacttca atccaaacgg     4020
agtacccggc tttgcagacg attgtgtacc attcaaaaaa gatcaatgca atattcggcc    4080
cgttgtttag tgagcttact aggcaattac tggacagtgt tgattcgagc agattttgt    4140 ttttcacaag aaagacacca gcgcagattg aggatttctt cggagatctc gacagtcatg    4200
tgccgatgga tgtcttggag ctggatatat caaaatacga caaatctcag aatgaattcc    4260
actgtgcagt agaatacgag atctggcgaa gattgggttt cgaagacttc ttgggagaag    4320
tttggaaaca agggcataga aagaccaccc tcaaggatta taccgcaggt ataaaaactt    4380
```

```
gcatctggta tcaaagaaag agcggggacg tcacgacgtt cattggaaac actgtgatca    4440
ttgctgcatg tttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga tacttttgcg    4620
gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt ctttttagaa gtttgtttat agatggctct agttgttaaa    4920
ggaaaagtga atatcaatga gtttatcgac ctgacaaaaa tggagaagat cttaccgtcg    4980
atgtttaccc ctgtaaagag tgttatgtgt tccaaagttg ataaaataat ggttcatgag    5040
aatgagtcat tgtcaggggt gaaccttctt aaaggagtta agcttattga tagtggatac    5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cattctcgga    5220
tcttactaca cagcagctgc aaagaaaaga tttcagttca aggtcgttcc caattatgct    5280
ataaccaccc aggacgcgat gagaaacgtc tggcaagttt tagttaatat tagaaatgtg    5340
aagatgtcag cgggtttctg tccgcttttct ctggagtttg tgtcggtgtg tattgtttat    5400
agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa agagtgatg tccgcaaagg gaaaaatagt    5580
agtagtgatc ggtcagtgcc gaacaagaac tatagaaatg ttaaggattt tggaggaatg    5640
agttttaaaa agaataattt aatcgatgat gattcggagg ctactgtcgc cgaatcggat    5700 tcgtttttaaa tagatcttac agtatcacta ctccatctca gttcgtgttc ttgtcattaa    5760
ttaaatggct agcaaaggag aagaactttt cactggagtt gtcccaattc ttgttgaatt    5820
agatggtgat gttaatgggc acaaattttc tgtcagtgga gagggtgaag gtgatgctac    5880
atacggaaag cttacactta aatttatttg cactactgga aaactacctg ttccatggcc    5940
aacacttgtc actactttct cttatggtgt tcaatgcttt tcccgttatc cggatcatat    6000
gaaacggcat gactttttca agagtgccat gcccgaaggt tatgtacagg aacgcactat    6060
atctttcaaa gatgacggga actacaagac gcgtgctgaa gtcaagtttg aaggtgatac    6120
ccttgttaat cgtatcgagt taaaaggtat tgattttaaa gaagatggaa acattctcgg    6180
acacaaactc gagtacaact ataactcaca caatgtatac atcacggcag acaaacaaaa    6240
gaatggaatc aaagctaact tcaaaattcg ccacaacatt gaagatggat ccgttcaact    6300
agcagaccat tatcaacaaa atactccaat tggcgatggc cctgtccttt taccagacaa    6360
ccattacctg tcgacacaat ctgccctttc gaaagatccc aacgaaaagc gtgaccacat    6420
ggtccttctt gagtttgtaa ctgctgctgg gattacacat ggcatggatg agctctacaa    6480
ataatgacac tcgaggggta gtcaagatgc ataataaata acggattgtg tccgtaatca    6540
cacgtggtgc gtacgataac gcatagtgtt tttccctcca cttaaatcga agggttgtgt    6600
cttggatcgc gcgggtcaaa tgtatatggt tcatatacat ccgcaggcac gtaataaagc    6660
gaggggttcg ggtcgaggtc ggctgtgaaa ctcgaaaagg ttccggaaaa caaaaaagag    6720
```

-continued

| | |
|---|---|
| agtggtaggt aatagtgtta ataataagaa aataaataat agtggtaaga aaggtttgaa | 6780 |
| agttgaggaa attgaggata atgtaagtga tgacgagtct atcgcgtcat cgagtacgtt | 6840 |
| ttaatcaata tgccttatac aatcaactct ccgagccaat ttgtttactt aagttccgct | 6900 |
| tatgcagatc ctgtgcagct gatcaatctg tgtacaaatg cattgggtaa ccagtttcaa | 6960 |
| acgcaacaag ctaggacaac agtccaacag caatttgcgg atgcctggaa acctgtgcct | 7020 |
| agtatgacag tgagatttcc tgcatcggat ttctatgtgt atagatataa ttcgacgctt | 7080 |
| gatccgttga tcacggcgtt attaaatagc ttcgatacta gaaatagaat aatagaggtt | 7140 |
| gataatcaac ccgcaccgaa tactactgaa atcgttaacg cgactcagag ggtagacgat | 7200 |
| gcgactgtag ctataagggc ttcaatcaat aatttggcta atgaactggt tcgtggaact | 7260 |
| ggcatgttca atcaagcaag ctttgagact gctagtggac ttgtctggac cacaactccg | 7320 |
| gctacttagc tattgttgtg agatttccta aaataaagtc actgaagact taaaattcag | 7380 |
| ggtggctgat accaaaatca gcagtggttg ttcgtccact taaatataac gattgtcata | 7440 |
| tctggatcca acagttaaac catgtgatgg tgtatactgt ggtatggcgt aaaacaacgg | 7500 |
| aaaagtcgct gaagacttaa aattcagggt ggctgatacc aaaatcagca gtggttgttc | 7560 |
| gtccacttaa aaataacgat tgtcatatct ggatccaaca gttaaaccat gtgatggtgt | 7620 |
| atactgtggt atggcgtaaa acaacggaga ggttcgaatc ctcccctaac cgcgggtagc | 7680 |
| ggccca | 7686 |

<210> SEQ ID NO 3
<211> LENGTH: 807
<212> TYPE: DNA
<213> ORGANISM: Nicotiana tabacum

<400> SEQUENCE: 3

| | |
|---|---|
| atggctctag ttgttaaagg aaaagtgaat atcaatgagt ttatcgacct gacaaaaatg | 60 |
| gagaagatct taccgtcgat gtttaccccct gtaaagagtg ttatgtgttc caaagttgat | 120 |
| aaaataatgg ttcatgagaa tgagtcattg tcagggggtga accttcttaa aggagttaag | 180 |
| cttattgata gtggatacgt ctgtttagcc ggtttggtcg tcacgggcga gtggaacttg | 240 |
| cctgacaatt gcagaggagg tgtgagcgtg tgtctggtgg acaaaaggat ggaaagagcc | 300 |
| gacgaggcca ctctcggatc ttactacaca gcagctgcaa agaaaagatt tcagttcaag | 360 |
| gtcgttccca attatgctat aaccacccag gacgcgatga aaaacgtctg gcaagtttta | 420 |
| gttaatatta gaaatgtgaa gatgtcagcg ggtttctgtc cgctttctct ggagtttgtg | 480 |
| tcggtgtgta ttgtttatag aaataatata aaattaggtt tgagagagaa gattacaaac | 540 |
| gtgagagacg gagggcccat ggaacttaca gaagaagtcg ttgatgagtt catggaagat | 600 |
| gtccctatgt cgatcaggct tgcaaagttt cgatctcgaa ccggaaaaaa gagtgatgtc | 660 |
| cgcaaaggga aaaatagtag tagtgatcgg tcagtgccga acaagaacta tagaaatgtt | 720 |
| aaggattttg gaggaatgag ttttaaaaag aataatttaa tcgatgatga ttcggaggct | 780 |
| actgtcgccg aatcggattc gttttaa | 807 |

<210> SEQ ID NO 4
<211> LENGTH: 807
<212> TYPE: DNA
<213> ORGANISM: Nicotiana tabacum

<400> SEQUENCE: 4

| | |
|---|---|
| atggctctag ttgttaaagg aaaagtgaat atcaatgagt ttatcgacct gacaaaaatg | 60 |

```
gagaagatct taccgtcgat gtttacccct gtaaagagtg ttatgtgttc caaagttgat      120
aaaataatgg ttcatgagaa tgagtcattg tcaggggtga accttcttaa aggagttaag      180
cttattgata gtggatacgt ctgtttagcc ggtttggtcg tcacgggcga gtggaacttg      240
cctgacaatt gcagaggagg tgtgagcgtg tgtctggtgg acaaaaggat ggaaagagcc      300
gacgaggcca ttctcggatc ttactacaca gcagctgcaa agaaaagatt tcagttcaag      360
gtcgttccca attatgctat aaccacccag gacgcgatga aaacgtctg gcaagttta       420 gttaatatta gaaatgtgaa gatgtcagcg gtttctgtc cgctttctct ggagtttgtg      480
tcggtgtgta ttgtttatag aaataatata aaattaggtt tgagagagaa gattacaaac      540
gtgagagacg gagggcccat ggaacttaca gaagaagtcg ttgatgagtt catggaagat      600
gtccctatgt cgatcaggct tgcaaagttt cgatctcgaa ccggaaaaaa gagtgatgtc      660
cgcaaaggga aaaatagtag tagtgatcgg tcagtgccga acaagaacta tagaaatgtt      720
aaggattttg gaggaatgag ttttaaaaag aataatttaa tcgatgatga ttcggaggct      780
actgtcgccg aatcggattc gttttaa                                         807
```

<210> SEQ ID NO 5
<211> LENGTH: 268
<212> TYPE: PRT
<213> ORGANISM: Nicotiana tabacum

<400> SEQUENCE: 5

```
Met Ala Leu Val Val Lys Gly Lys Val Asn Ile Asn Glu Phe Ile Asp
1               5                   10                  15

Leu Thr Lys Met Glu Lys Ile Leu Pro Ser Met Phe Thr Pro Val Lys
            20                  25                  30

Ser Val Met Cys Ser Lys Val Asp Lys Ile Met Val His Glu Asn Glu
        35                  40                  45

Ser Leu Ser Gly Val Asn Leu Leu Lys Gly Val Lys Leu Ile Asp Ser
    50                  55                  60

Gly Tyr Val Cys Leu Ala Gly Leu Val Val Thr Gly Glu Trp Asn Leu
65                  70                  75                  80

Pro Asp Asn Cys Arg Gly Gly Val Ser Val Cys Leu Val Asp Lys Arg
                85                  90                  95

Met Glu Arg Ala Asp Glu Ala Thr Leu Gly Ser Tyr Tyr Thr Ala Ala
            100                 105                 110

Ala Lys Lys Arg Phe Gln Phe Lys Val Val Pro Asn Tyr Ala Ile Thr
        115                 120                 125

Thr Gln Asp Ala Met Lys Asn Val Trp Gln Val Leu Val Asn Ile Arg
    130                 135                 140

Asn Val Lys Met Ser Ala Gly Phe Cys Pro Leu Ser Leu Glu Phe Val
145                 150                 155                 160

Ser Val Cys Ile Val Tyr Arg Asn Asn Ile Lys Leu Gly Leu Arg Glu
                165                 170                 175

Lys Ile Thr Asn Val Arg Asp Gly Gly Pro Met Glu Leu Thr Glu Glu
            180                 185                 190

Val Val Asp Glu Phe Met Glu Asp Val Pro Met Ser Ile Arg Leu Ala
        195                 200                 205

Lys Phe Arg Ser Arg Thr Gly Lys Lys Ser Asp Val Arg Lys Gly Lys
    210                 215                 220

Asn Ser Ser Ser Asp Arg Ser Pro Asn Lys Asn Tyr Arg Asn Val
225                 230                 235                 240
```

```
Lys Asp Phe Gly Gly Met Ser Phe Lys Lys Asn Asn Leu Ile Asp Asp
                245                 250                 255

Asp Ser Glu Ala Thr Val Ala Glu Ser Asp Ser Phe
            260                 265

<210> SEQ ID NO 6
<211> LENGTH: 268
<212> TYPE: PRT
<213> ORGANISM: Nicotiana tabacum

<400> SEQUENCE: 6

Met Ala Leu Val Val Lys Gly Lys Val Asn Ile Asn Glu Phe Ile Asp
1               5                   10                  15

Leu Thr Lys Met Glu Lys Ile Leu Pro Ser Met Glu Thr Pro Val Lys
                20                  25                  30

Ser Val Met Cys Ser Lys Val Asp Lys Ile Met Val His Glu Asn Glu
            35                  40                  45

Ser Leu Ser Gly Val Asn Leu Leu Lys Gly Val Lys Leu Ile Asp Ser
        50                  55                  60

Gly Tyr Val Cys Leu Ala Gly Leu Val Val Thr Gly Glu Trp Asn Leu
65                  70                  75                  80

Pro Asp Asn Cys Arg Gly Gly Val Ser Val Cys Leu Val Asp Lys Arg
                85                  90                  95

Met Glu Arg Ala Asp Glu Ala Ile Leu Gly Ser Tyr Tyr Thr Ala Ala
            100                 105                 110

Ala Lys Lys Arg Phe Gln Phe Lys Val Val Pro Asn Tyr Ala Ile Thr
        115                 120                 125

Thr Gln Asp Ala Met Arg Asn Val Trp Gln Val Leu Val Asn Ile Arg
130                 135                 140

Asn Val Lys Met Ser Ala Gly Phe Cys Pro Leu Ser Leu Glu Phe Val
145                 150                 155                 160

Ser Val Cys Ile Val Tyr Arg Asn Asn Ile Lys Leu Gly Leu Arg Glu
                165                 170                 175

Lys Ile Thr Asn Val Arg Asp Gly Gly Pro Met Glu Leu Thr Glu Glu
            180                 185                 190

Val Val Asp Glu Phe Met Glu Asp Val Pro Met Ser Ile Arg Leu Ala
        195                 200                 205

Lys Phe Arg Ser Arg Thr Gly Lys Lys Ser Asp Val Arg Lys Gly Lys
210                 215                 220

Asn Ser Ser Ser Asp Arg Ser Val Pro Asn Lys Asn Tyr Arg Asn Val
225                 230                 235                 240

Lys Asp Phe Gly Gly Met Ser Phe Lys Lys Asn Asn Leu Ile Asp Asp
                245                 250                 255

Asp Ser Glu Ala Thr Val Ala Glu Ser Asp Ser Phe
            260                 265
```

VIRAL EXPRESSION VECTORS

CROSS-REFERENCE TO RELATED APPLICATION

This application claims the priority benefit of provisional U.S. Patent Application Ser. No. 60/132,697, filed May 4, 1999, pending, which is hereby incorporated herein by reference in its entirety.

TECHNICAL FIELD

This invention is in the field of plant virology. Specifically, the invention relates to the synthesis of nucleic acid sequences encoding an altered viral movement protein, construction of viral vectors expressing such protein, and generation of host plants infected by the viral vectors. The viral vectors permit rapid local and systemic invasion of a host, and allow stable expression of a transgene of interest.

BACKGROUND OF THE INVENTION

In the last fifteen years, considerable progress has been made in expressing foreign genes in plants. Foreign proteins are now routinely produced in many plant species for modification of the plant or for production of proteins for use after extraction. Vectors for the genetic manipulation of plants have been derived from several naturally occurring plant viruses. For the production of specific proteins, transient expression of foreign genes in plants using virus-based vectors has several advantages. Products of plant viruses are among the highest produced proteins in plants. Often a viral gene product is the major protein produced in plant cells during virus replication. Many viruses are able to systemically move from an initial infection site to almost all cells of the plant. Because of these reasons, plant viruses have been developed into efficient transient expression vectors for foreign genes in plants. Viruses of multi-cellular plants are relatively small, probably due to the size limitation in the pathways that allow viruses to move to adjacent cells in the systemic infection of entire plants. One such plant virus upon which plant expression vectors are based is TMV (tobacco mosaic virus). TMV is the type member of the tobamovirus group. TMV has straight tubular virions of approximately 300×18 nm with a 4 nm-diameter hollow canal consisting of approximately 2000 units of a single capsid protein wound helically around a single RNA molecule. Virion particles are 95% protein and 5% RNA by weight. The genome of TMV is composed of a single-stranded RNA of 6395 nucleotides containing five large ORFs. Expression of each gene is regulated independently. The virion RNA serves as the messenger RNA (mRNA) for the 5' genes, encoding the 126 kDa replicase subunit and the overlapping 183 kDa replicase subunit that is produced by read through of an amber stop codon approximately 5% of the time. Expression of the internal genes is controlled by different promoters on the minus-sense RNA that direct synthesis of 3'-coterminal subgenomic mRNAs which are produced during replication. A detailed description of tobamovirus gene expression and life cycle can be found, among other places, in Dawson and Lehto, *Advances in Virus Research* 38:307–342 (1991).

Thus, it is of scientific and commercial interest to provide new and improved vectors for the genetic manipulation of plants.

SUMMARY OF THE INVENTION

A principal aspect of the present invention is the design of a recombinant viral vector expressing an altered movement protein and altered 126/183 viral proteins to affect stable expression of a transgene in a plant host.

Accordingly, the present invention provides an isolated nucleic acid sequence encoding an altered viral movement protein having the amino acid sequence shown in SEQ ID NOS.: 5 and 6 and altered 126/183 viral proteins. In one aspect, the isolated nucleic acid sequence is essentially identical to the sequence shown in SEQ ID NOS.: 3 and 4, and it contains a Thymine ( T) or Uracil (U) residue at position 5213 and Guanine (G) residue at 5303 as shown in FIG. 1A. In another aspect, the isolated nucleic acid sequence is identical to the sequence shown in SEQ ID NOS.: 3 and 4. The alteration of the 30K movement protein and alteration of the 126/183 viral proteins results in an enhanced ability to facilitate stabilization of a transgene contained in a viral vector.

In a separate embodiment, the present invention provides a viral vector comprising the nucleic acid sequence encoding an altered viral movement protein having the amino acid sequence shown in SEQ ID NOS.: 5 and 6 and altered 126/183 viral proteins. In one aspect, the viral vector exhibits an enhanced ability compared to a control viral vector to stabilize a transgene contained in the vector. Preferably, the vector is a tobacco mosaic viral vector. A particularly preferred vector is designated BSG1057 (deposited with American Type Culture Collection, 10801 University Blvd., Manassas, Va. 20110, having accession number 203981, which was deposited on Apr. 29, 1999).

In a separate aspect within this embodiment, the viral vector comprises a transgene of interest. Preferably the transgene is a non-viral gene encoding a protein selected from the group consisting of a membrane protein, a cytosolic protein, a secreted protein, a nuclear protein, and a chaperon protein.

The present invention also provides a cell transformed with a subject viral vector. The transformed cell may be animal or plant. Preferably, the cell is a plant cell. The present invention further provides a transgenic plant comprising the viral vector. Preferred transgenic plant may, for example, be *Nicotiana benthamiana* or *Nicotiana tabacum*, but others may be just as readily substituted by one of skill in the art.

BRIEF DESCRIPTION OF THE DRAWINGS

FIG. 1A depicts a comparison of the nucleotide sequences encoding an altered movement protein contained in the vector BSG1057 (SEQ ID NO.: 4) and the wildtype movement protein contained in the vector BSG1037 (SEQ ID NO.: 3). Sequence identities are indicated by *, and mismatches are indicated by -. FIG. 1B depicts a second portion of the comparison depicted in FIG. 1A.

FIG.2 depicts a comparison of the amino acid sequences encoding an altered movement protien contained in the vector BSG1057 (SEQ ID NO.: 6) and the wildtype movement protein contained in the vector BSG1037 (SEQ ID NO.: 5). Sequence Identities are indicated by *, and mismatches are indicated by -.

FIG. 5A is the complete sequence of BSG1037 (SEQ ID NO.: 1). FIGS. 5B, 5C, 5D, and 5E depict second, third, fourth and fifth portions, respectively, of the complete sequence of BSG1037 (SEQ ID NO.: 1).

FIG. 6A is the complete sequence of BSG1057 (SEQ ID NO.: 2). FIGS. 6B, 6C, 6D, and 6E depict second, third, fourth and fifth portions, respectively, of the complete sequence of BSG1057 (SEQ ID NO.: 2).

FIG. 7 is a schematic map of locations of mutations in BSG1057.

MODES FOR CARRYING OUT THE INVENTION

Figure 3:
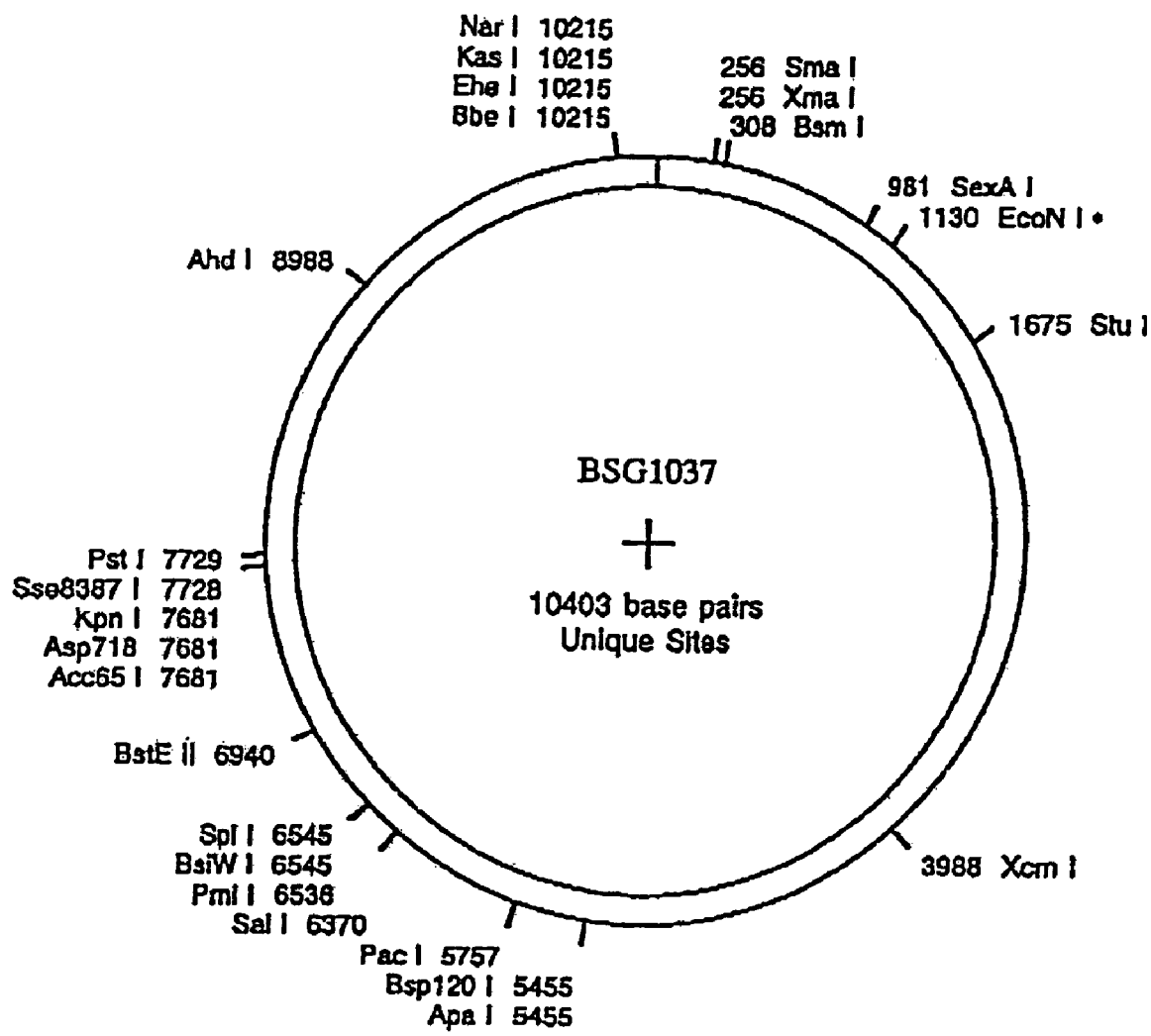
FIG. 3 is a schematic representation of the restriction sites of the vector BSG1037.
Figure 4:
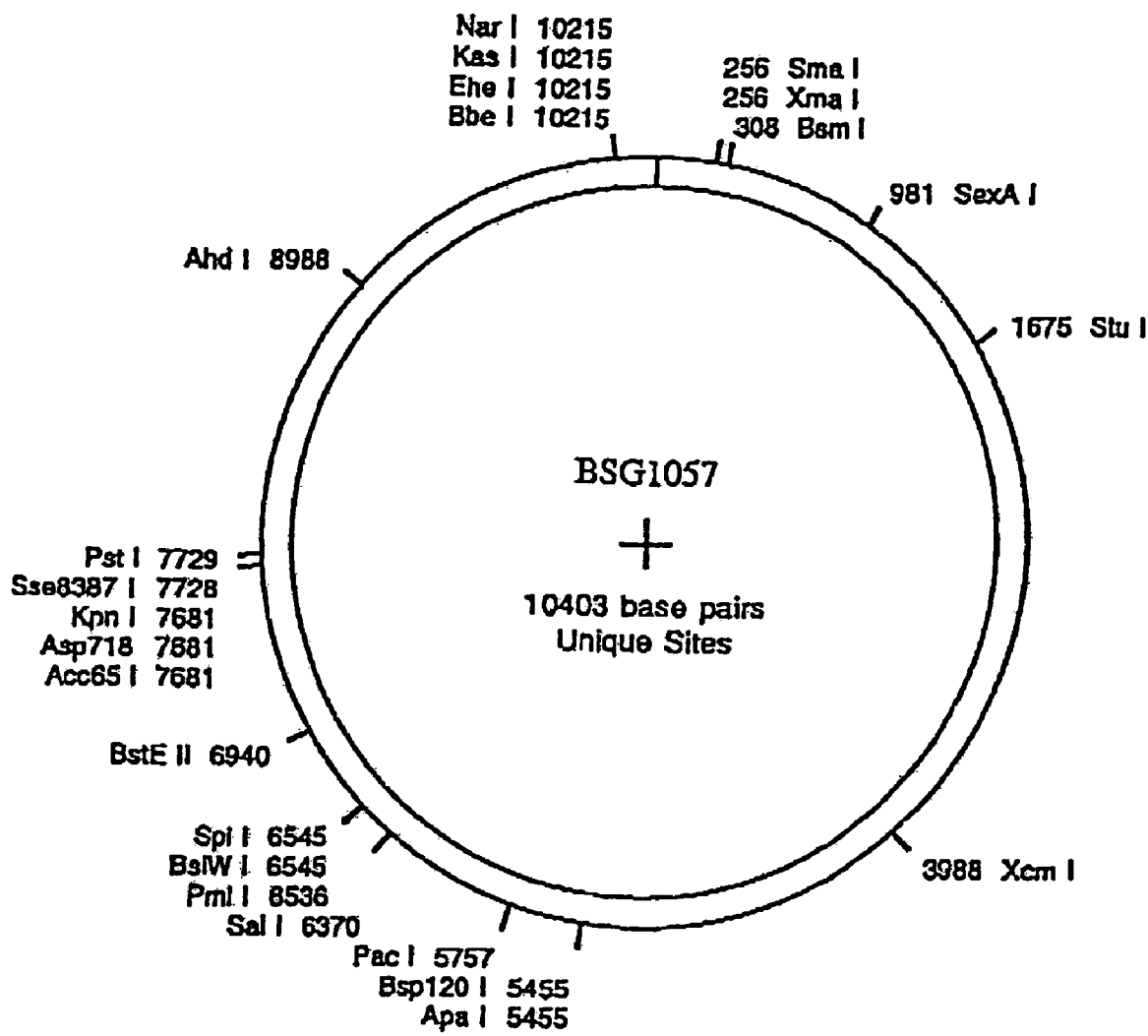
FIG. 4 is a schematic representation of the restriction sites of the vector BSG1057.
Figure 8:
FIG. 8 shows *N. benthamiana* plants at 20 days postinoculation. There are four columns of five plants. The first column on the left shows plants inoculated with first passage BSG1037. Column 2 is seventh passage BSG1037, Column 3 is first passage BSG1057, Column 4 is seventh passage BSG1057.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains. For example, the general teaching for constructing viral plant vectors and using them to systemically infect plants and express heterologous proteins therefrom is disclosed in U.S. Pat. Nos. 5,316,931; 5,977,438; 5,889,191; 5,889,190; 5,866,785 and 5,816,653, the entire disclosures of which are hereby incorporated herein by reference.

General Techniques:

The practice of the present invention will employ, unless otherwise indicated, conventional techniques of immunology, biochemistry, chemistry, molecular biology, microbiology, cell biology, genomics and recombinant DNA, which are within the skill of the art. See, e.g., Matthews, PLANT VIROLOGY, $3^{rd}$ edition (1991); Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

DEFINITIONS

A "plant cell" refers to the structural and physiological unit of plants, consisting of a protoplast and the cell wall.

A "protoplast" is an isolated cell without cell walls, having the potency for regeneration into cell culture, tissue or whole plant.

A "host" encompasses cell, tissue or organism capable of replicating a vector or viral nucleic acid and which is capable of being infected by a virus containing the viral vector or viral nucleic acid. This term is intended to include prokaryotic and eukaryotic cells, organs, tissues, organisms, or in vitro extracts thereof, where appropriate. A preferred host cell is a plant cell.

The term "infection" refers to the process of transferring or the ability of a virus to transfer its nucleic acid to a host, wherein the viral nucleic acid is replicated, viral proteins are synthesized, or new viral particles assembled.

The "movement protein" of tobacco mosaic virus is a noncapsid protein required for cell-to-cell movement of the RNA replicons or viruses in plants.

The terms "nucleic acid sequence", "polynucleotide", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A "gene" refers to a polynucleotide containing at least one open reading frame that is capable of encoding a particular protein after being transcribed and translated.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as gene product. If the polynucleotide is derived from genomic DNA, expression may include splicing of the mRNA in an eukaryotic cell.

In the context of polynucleotides, a "linear sequence" or a "sequence" is an order of nucleotides in a polynucleotide in a 5' to 3' direction in which residues that neighbor each other in the sequence are contiguous in the primary structure of the polynucleotide.

A linear sequence of nucleotides is "essentially identical" to another linear sequence, if both sequences are capable of hybridizing to form a duplex with the same complementary polynucleotide. Sequences that hybridize under conditions of greater stringency are more preferred. It is understood that hybridization reactions can accommodate insertions, deletions, and substitutions in the nucleotide sequence. Thus, linear sequences of nucleotides can be essentially identical even if some of the nucleotide residues do not precisely correspond or align. In general, essentially identical sequences of about 40 nucleotides in length will hybridize at about 30° C. in 10×SSC (0.15 M NaCl, 15 mM citrate buffer); preferably, they will hybridize at about 40° C. in 6×SSC; more preferably, they will hybridize at about 50° C. in 6×SSC; even more preferably, they will hybridize at about 60° C. in 6×SSC, or at about 40° C. in 0.5×SSC, or at about 30° C. in 6×SSC containing 50% formamide; still more preferably, they will hybridize at 40° C. or higher in 2×SSC or lower in the presence of 50% or more formamide. It is understood that the rigor of the test is partly a function of the length of the polynucleotide; hence shorter polynucleotides with the same homology should be tested under lower stringency and longer polynucleotides should be tested under higher stringency, adjusting the conditions accordingly. The relationship between hybridization stringency, degree of sequence identity, and polynucleotide length is known in the art and can be calculated by standard formulae; see, e.g., Meinkoth et al. Sequences that correspond or align more closely to the invention disclosed herein are comparably more preferred. Generally, essentially identical sequences are at least about 50% identical with each other, after alignment of the homologous regions. Preferably, the sequences are at least about 60% identical; more preferably, they are at least about 70% identical; more preferably, they are at least about 80% identical; more preferably, the sequences are at least about 90% identical; even more preferably, they are at least 95% identical; still more preferably, the sequences are 100% identical.

In determining whether polynucleotide sequences are essentially identical, a sequence that preserves the functionality of the polynucleotide with which it is being compared is particularly preferred. Functionality may be established by different criteria, such as ability to hybridize with a target polynucleotide, and whether the polynucleotide encodes an identical or essentially identical polypeptides. Thus, nucleotide substitutions which cause a non-conservative substitution in the encoded polypeptide are preferred over nucleotide substitutions that create a stop codon; nucleotide substitutions that cause a conservative substitution in the encoded polypeptide are more preferred, and identical nucleotide sequences are even more preferred. Insertions or deletions in the polynucleotide that result in insertions or deletions in the polypeptide are preferred over those that result in the down-stream coding region being rendered out of phase.

The term "hybridize" as applied to a polynucleotide refers to the ability of the polynucleotide to form a complex that is stabilized via hydrogen bonding between the bases of the nucleotide residues in a hybridization reaction. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these.

The terms "cytosolic", "nuclear" and "secreted" as applied to cellular proteins specify the extracellular and/or subcellular location in which the cellular protein is mostly localized. Certain proteins are "chaperons", capable of translocating back and forth between the cytosol and the nucleus of a cell.

A "control" is an alternative subject or sample used in an experiment for comparison purpose. For example, where the purpose of the experiment is to ascertain whether a viral vector carrying an altered movement protein possesses an enhanced ability in systemic invasion of a host plant, it is generally preferable to use a control viral vector (e.g. BSG1037 shown in FIGS. 1–2) expressing the wildtype altered movement protein (e.g. 1037 sequence shown in FIG. 2).

A "cell line" or "cell culture" denotes bacterial, plant, insect or higher eukaryotic cells grown or maintained in vitro. The descendants of a cell may not be completely identical (either morphologically, genotypically, or phenotypically) to the parent cell.

A "vector" refers to a recombinant plasmid or virus that comprises a polynucleotide to be delivered into a host cell, either in vitro or in vivo. The polynucleotide to be delivered may comprise a coding sequence of interest in gene therapy nucleic acid molecule, preferably self-replicating, which transfers an inserted nucleic acid molecule into and/or between host cells. The term includes vectors that function primarily for insertion of a DNA or RNA into a cell, replication of vectors that function primarily for the replication of DNA or RNA, and expression vectors that function for transcription and/or translation of the DNA or RNA. Also included are vectors that provide more than one of the above functions.

A "replicon" refers to a polynucleotide comprising an origin of replication (generally referred to as an ori sequence) which allows for replication of the polynucleotide in an appropriate host cell. Examples of replicons include episomes (such as plasmids), as well as chromosomes (such as the nuclear or mitochondrial chromosomes).

A "transcription unit" is a DNA segment capable of directing transcription of a gene or fragment thereof. Typically, a transcription unit comprises a promoter operably linked to a gene or a DNA fragment that is to be transcribed, and optionally regulatory sequences located either upstream or downstream of the initiation site or the termination site of the transcribed gene or fragment.

Nucleic Acids of the Present Invention

The present invention encompasses a recombinant viral vector expressing an altered movement protein and altered 126/183 viral proteins to effect stable expression of a transgene in a plant host. Distinguished from the previously described movement protein, the altered protein contains two amino acid substitutions (replacing the threonine residue at position 104 with isoleucine, and replacing the lysine residue at position 134 with arginine, see FIG. 2). The altered viral vector exhibits an enhanced ability to facilitate stabilization of a transgene contained in a virus that expresses the altered movement protein.

In one embodiment, the present invention provides an isolated nucleic acid sequence encoding an altered viral movement protein having the amino acid sequence shown in SEQ ID NOS.: 5 and 6 and altered 126/183 viral proteins. In one aspect within this embodiment, the isolated nucleic acid sequence of the movement protein is essentially identical to the sequence shown in SEQ ID NO. 3, and it contains a Thymine (T) or Uracil (U) residue at position 5213 and Guanine (G) residue at 5303 as shown in FIG. 1A. As used herein, a linear sequence of nucleotides is "essentially identical" to another linear sequence, if both sequences are capable of hybridizing to form a duplex with the same complementary polynucleotide.

Hybridization can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. In general, a low stringency hybridization reaction is carried out at about 40° C. in 6×SSC or a solution of equivalent ionic strength/temperature. A moderate stringency hybridization is typically performed at about 50° C. in 6×SSC, and a high stringency hybridization reaction is generally performed at about 60° C. in 6×SSC. The essentially identical nucleic acid sequences embodiment in the invention encompass all sequences encoding modified movement proteins containing conservative or non-conservative substitutions that do not significantly affect the claimed structural characteristics (i.e.

retain the substitution of isoleucine for threonine$_{104}$, and arginine for lysine$_{134}$). Modification of polypeptides by altering their corresponding nucleic acid sequences is routine practice in the art. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. Changes in nucleic acid sequence that do not change the encoded amino acid sequence are generally preferred.

The recombinant viral vector embodiment of this invention comprises a nucleic acid sequence encoding the above-described viral movement protein.

In one embodiment, a nucleic acid is introduced into a plant host. Preferably, the nucleic acid may be introduced by way of a viral nucleic acid, using technques known in the art, and preferably the techniques disclosed in U.S. Pat. Nos. 5,316,931; 5,977,438; 5,889,191; 5,889,190; 5,866,785 and 5,816,653, the entire disclosures of which are hereby incorporated herein by reference. Such recombinant viral nucleic acids are stable for the maintenance and transcription of such normative sequences in the plant host.

BSG1057 (SEQ ID NO.:2) is a mutant version of BSG1037 (SEQ ID NO.:1). The complete sequences of BSG1057 and BSG1037 are shown in FIG. 5 and FIG. 6. BSG1037 has improved insert retention properties.

The difference between these two virus vectors is best demonstrated with the Green Fluorescent Protein (GFP) reporter gene. Both BSG1037 and BSG1057 express GFP which can be visualized under long wave UV light by its green fluorescence. The presence of GFP activity identifies those cells in which the recombinant virus is expressing genes.

*Nicotiana benthamiana* plants inoculated with BSG1037 and BSG1057 were observed under long wave UV light at approximately 4 to 5 days post inoculation. The GFP spots on the leaves of plants inoculated with the BSG1057 virus were noticeably larger than the GFP spots on the leaves of plants inoculted with the BSG1037 virus, indicating the 1057 virus moves cell to cell faster than BSG1037.

Sequence Comparison Between BSG1037 and BSG1057

The specific nucleotide changes between 1037 and 1057 are listed in the table below. In those cases where the nucleotide change resulted in an amino acid change, that change is noted (using the single letter code).

| nt position | 1037 nt | 1057 nt | 1037AA | 1057 AA |
|---|---|---|---|---|
| 1138 | A | G | E | G |
| 1268 | T | C | No AA changes | |
| 2382 | A | G | K | E |
| 3632 | G | A | No AA changes | |
| 5213 | C | T | T | I |
| 5303 | A | G | K | R |
| 5896 | C | A | No AA changes | |

126/183 refers to the 126/183 viral proteins.
MP refers to the movement protein.

The transgene transcribed by the vector of present invention can be any gene expressed in a biological entity. The selection of transgene is determined largely by the intended purpose of the vector. Preferably the transgene is a non-viral gene selected from the group consisting of a membrane protein, a cytosolic protein, a secreted protein, a nuclear protein, and a chaperon protein.

The vectors embodied in this invention can be obtained using recombinant cloning methods and/or by chemical synthesis. A vast number of recombinant cloning techniques such as PCR, restriction endonuclease digestion and ligation are well known in the art, and need not be described in detail herein. One skilled in the art can also use the sequence data provided herein or that in the public or proprietary databases to obtain a desired vector by any synthetic means available in the art.

Host Cell and Transgenic Organisms of the Present Invention:

The invention provides host cells transformed with the viral vectors described above. The host cells may be animal or plant, but plant hosts are preferred. The viral vectors containing a transgene of interest can be introduced into a suitable eukaryotic cell by any of a number of appropriate means, including electroporation, transfection employing calcium chloride, rubidium chloride, calcium phosphate, DEAE-dextran, or other substances; microprojectile bombardment; lipofection; and infection (where the vector is coupled to an infectious agent). The choice of introducing vectors will often depend on features of the host cell.

For plant cells, a variety of techniques derived from these general methods is available in the art. See, for example, U.S. Pat. Nos. 5,316,931; 5,977,438; 5,889,191; 5,889,190; 5,866,785 and 5,816,653. The host cells may be in the form of whole plants, isolated cells or protoplasts. Illustrative procedures for introducing vectors into plant cells include *Agrobacterium*-mediated plant transformation, protoplast transformation, gene transfer into pollen, injection into reproductive organs and injection into immature embryos, leaf abrasion, abrasion in solution, high velocity water spray, and other injury of a host as well as imbibing host seeds with water containing the recombinant viral RNA or recombinant plant virus. As is evident to one skilled in the art, each of these methods has distinct advantages and disadvantages. Thus, one particular method of introducing genes into a particular plant species may not necessarily be the most effective for another plant species.

*Agrobacterium tumefaciens*-mediated transfer is a widely applicable system for introducing genes into plant cells because the DNA can be introduced into whole plant tissues, bypassing the need for regeneration of an intact plant from a protoplast. The use of *Agrobacterium*-mediated expression vectors to introduce DNA into plant cells is well known in the art. This technique makes use of a common feature of *Agrobacterium* which colonizes plants by transferring a portion of their DNA (the T-DNA) into a host cell, where it becomes integrated into nuclear DNA. The T-DNA is defined by border sequences which are 25 base pairs long, and any DNA between these border sequences is transferred to the plant cells as well. The insertion of a recombinant plant viral nucleic acid between the T-DNA border sequences results in transfer of the recombinant plant viral nucleic acid to the plant cells, where the recombinant plant viral nucleic acid is replicated, and then spreads systemically through the plant. Agro-infection has been accomplished with potato spindle tuber viroid (PSTV) (Gardner et al., *Plant Mol. Biol.* 6:221 (1986); CaV (Grimsley et al., and Lazarowitz, S., *Nucl. Acids Res.* 16:229 (1988)) *digitaria* streak virus (Donson et al., *Virology* 162:248 (1988)), wheat dwarf virus, and tomato golden mosaic virus (TGMV). Therefore, agro-infection of a susceptible plant could be accomplished with a virion containing a recombinant plant viral nucleic acid based on the nucleotide sequence of any of the above viruses. Particle bombardment or electrosporation or any other methods known in the art may also be used.

Because not all plants are natural hosts for *Agrobacterium*, alternative methods such as transformation of protoplasts may be employed to introduce the subject vectors into the host cells. For certain monocots, transformation of the plant protoplasts can be achieved using methods based on calcium phosphate precipitation, polyethylene glycol treatment, electroporation, and combinations of these treatments. See, for example, Potrykus et al., *Mol. Gen. Genet.,* 199: 169–177 (1985); Fromm et al., *Nature,* 319:791 (1986); and Callis et al., *Genes and Development,* 1:1183 (1987). Applicability of these techniques to different plant species may depend upon the feasibility to regenerate that particular plant species from protoplasts. A variety of methods for the regeneration of cereals from protoplasts are known in the art.

In addition to protoplast transformation, particle bombardment is an alternative and convenient technique for delivering the invention vectors into a plant host cell. Specifically, the plant cells may be bombarded with microparticles coated with a plurality of the subject vectors. Bombardment with DNA-coated microprojectiles has been successfully used to produce stable transformants in both plants and animals (see, for example, Sanford et al. (1993) *Methods in Enzymology,* 217:483–509). Microparticles suitable for introducing vectors into a plant cell are typically made of metal, preferably tungsten or gold. These microparticles are available for example, from BioRad (e.g., Bio-Rad's PDS-1000/He). Those skilled in the art will know that the particle bombardment protocol can be optimized for any plant by varying parameters such as He pressure, quantity of coated particles, distance between the macrocarrier and the stopping screen and flying distance from the stopping screen to the target.

Vectors can also be introduced into plants by direct DNA transfer into pollen as described by Zhou et al., Methods in Enzymology, 101: 433 (1983). Other techniques for introducing nucleic acids into a plant cell include:
(a) Hand Inoculations. Hand inoculations are performed using a neutral pH, low molarity phosphate buffer, with the addition of celite or carborundum (usually about 1%). One to four drops of the preparation is put onto the upper surface of a leaf and gently rubbed.
(b) Mechanized Inoculations of Plant Beds. Plant bed inoculations are performed by spraying (gas-propelled) the vector solution into a tractor-driven mower while cutting the leaves. Alternatively, the plant bed is mowed and the vector solution sprayed immediately onto the cut leaves.
(c) High Pressure Spray of Single Leaves. Single plant inoculations can also be performed by spraying the leaves with a narrow, directed spray (50 psi, 6–12 inches from the leaf) containing approximately 1% carborundum in the buffered vector solution.
(d) Vacuum Infiltration. Inoculations may be accomplished by subjecting a host organism to a substantially vacuum pressure environment in order to facilitate infection.

Once introduced into a suitable host cell, expression of the transgene can be determined using any assay known in the art. For example, the presence of transcribed sense or anti-sense strands of the transgene can be detected and/or quantified by conventional hybridization assays (e.g. Northern blot analysis), amplification procedures (e.g. RT-PCR), SAGE (U.S. Pat. No. 5,695,937), and array-based technologies (see e.g. U.S. Pat. Nos. 5,405,783, 5,412,087 and 5,445,934).

Expression of the transgene can also be determined by examining the protein product. A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and PAGE-SDS.

In general, determining the protein level involves (a) providing a biological sample containing polypeptides; and (b) measuring the amount of any immunospecific binding that occurs between an antibody reactive to the trangene product and a component in the sample, in which the amount of immunospecific binding indicates the level of expressed proteins. Antibodies that specifically recognize and bind to the protein products of the transgene are required for immunoassays. These may be purchased from commercial vendors or generated and screened using methods well known in the art. See Harlow and Lane (1988) supra. and Sambrook et al. (1989) supra. The sample of test proteins can be prepared by homogenizing the eukaryotic transformants (e.g. plant cells) or their progenies made therefrom, and optionally solubilizing the test protein using detergents, preferably non-reducing detergents such as triton and digitonin. The binding reaction in which the test proteins are allowed to interact with the detecting antibodies may be performed in solution, or on a solid tissue sample, for example, using tissue sections or solid support that has been immobilized with the test proteins. The formation of the complex can be detected by a number of techniques known in the art. For example, the antibodies may be supplied with a label and unreacted antibodies may be removed from the complex; the amount of remaining label thereby indicating the amount of complex formed. Results obtained using any such assay on a sample from a plant transformant or a progeny thereof is compared with those from a non-transformed source as a control.

The eukaryotic host cells of this invention are grown under favorable conditions to effect transcription of the transgene. The host cells may also be employed to generate transgenic organisms such as transgenic plants comprising the recombinant DNA vectors of the present invention. Preferred host cells are those having the propensity to regenerate into tissue or a whole organisms. Examples of these preferred host cells include certain plant cells exemplified herein.

Accordingly, this invention provides transgenic plants carrying the subject vectors. The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil.

The regeneration of plants containing the subject vector introduced by *Agrobacterium tumefaciens* from leaf explants can be achieved as described by Fraley et al., *Proc. Natl. Acad. Sci. USA.,* 80:4803 (1983). In this procedure, transformants are grown in the presence of a selection agent and in a medium that induces the regeneration of shoots in the plant species being transformed. This procedure typically produces shoots within two to four weeks and these transformant shoots are then transferred to an appropriate root-inducing medium containing the selective agent and an antibiotic to prevent bacterial growth. Transformant shoots that rooted in the presence of the selective agent to form plantlets are then transplanted to soil to allow the production of roots. These procedures will vary depending upon the particular plant species employed, as is apparent to one of ordinary skill in the art.

A population of progeny can be produced from the first and second transformants of a plant species by methods well known in the art including cross fertilization and asexual reproduction. Transgenic plants embodied in the present invention are useful for production of desired proteins, and as test systems for analysis of the biological functions of a gene.

EXAMPLES

Tobacco plants inoculated with the viruses BSG1037 or BSG1057 express the reporter gene (GFP) in cells that are infected with either virus. The reporter gene activity (indicative of the presence of virus) is easily observed by illuminating plants with long wave UV light. Viruses that lose expression of the inserted gfp gene no longer accumulate the GFP protein and do not exhibit GFP fluorescence under UV illumination.

In order to assess the stability of expression of a foreign gene in the new vector, the gfp gene was introduced into the standard vector (giving rise to BSG1037) and the improved vector (giving rise to BSG1057). RNA transcripts of these constructs was generated and used to inoculate *Nicotiana benthamiana* plants. At about 7 days postinoculation, extensive systemic GFP expression was observed. GFP-expressing tissue was harvested, ground in phosphate buffer, the cellular debris removed by low-speed centrifugation, and the resulting "green juice" supernatant solution used to inoculate a new set of *N. benthamiana* plants. Systemic tissue was again harvested at about 7 days and the resulting green juice used to serial passage the virus. The procedure was used to serial passage the viruses a total of 7 times. A comparison was then initiated in which *N. benthamiana* plants were inoculated in parallel with the first passage green juice and the seventh passage green juice for BSG1037 and BSG1057. The first passage virus gave excellent systemic expression of GFP beginning about 4 days post inoculation. The BSG1037 seventh passage virus gave little systemic GFP expression and strong visual TMV mosaic symptoms characteristic of a vector that has lost most or all of the inserted sequence. In contrast, the BSG1057 seventh passage virus still gave excellent systemic GFP expression and the mild visual viral symptoms characteristic of a vector retaining its inserted gene.

At 20 days post inoculation, the plants were cut 2 inches above the soil line and allowed to regrow. Plants were monitored as to the accumulation of GFP protein in the new systemic tissue up to 3 weeks post cutting. Plants containing the BSG 1037 virus (both first and seventh passage) showed very little GFP in regrowth tissues, while showing extensive virus symptoms. This result indicates that the virus population was dominated by viruses that have recombinationally lost the genetic insertion. Plants containing BSG1057 (both first and seventh passage) showed good systemic invasion in re-growth tissue. This indicates superior genetic stability of the foreign gene insertion, gfp gene, in BSG1057 compared with BSG1037.

This increased genetic stability of foreign genes was also seen using two additional gene insertions: interferon gamma from chickens and human alpha galactosidase A. Serial passage experiments of either gene in BSG1037 virus preparations showed variable production of product in plants, while comparable experiments in BSG1057 showed more uniform product accumulation in plants. These experiments indicate that the BSG1057 retains foreign gene insertions through multiple passages to a greater extent.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method for stable expression of a transgene in a plant host cell, the method comprising:
   a) providing a viral vector suitable for introduction into the plant host cell, wherein the viral vector encodes an altered viral movement protein and a transgene, and wherein the encoded altered movement protein comprises SEQ ID NO:6;
   b) introducing the viral vector into the plant host cell to produce a transformant host cell;
   c) growing the transformant host cell under favorable conditions to effect transcription of the transgene; and
   d) regenerating a transformant host cell into a transformant tissue or whole organism, thereby providing stable expression of the transgene.

2. The method of claim 1, wherein the viral vector further comprises sequences encoding altered 126/183 viral proteins, wherein the altered 126/183 viral proteins enhance stabilization of the transgene encoded by the viral vector.

3. The method of claim 2, wherein the altered 126/183 viral proteins have nucleic acid alterations at nucleotide positions 1138, 1268, 2382, and 3632 as shown in SEQ ID NO:2.

4. The method of claim 2, wherein the viral vector comprises SEQ ID NO:2.

5. The method of claim 1, wherein the plant host cell comprises a whole plant, an isolated plant cell, or a protoplast.

6. The method of claim 1, wherein the plant host cell comprises a natural host for *Agrobacterium*, and wherein introducing the viral vector comprises performing *Agrobacterium*-mediated plant transformation.

7. The method of claim 1, wherein the plant host cell comprises a species that can be regenerated from a protoplast, and wherein introducing the viral vector comprises performing protoplast transformation.

8. The method of claim 1, wherein the plant host cell comprises a monocot, and wherein introducing the viral vector comprises performing calcium phosphate precipitation, polyethylene glycol treatment, electroporation, or a combination thereof.

9. The method of claim 1, wherein introducing the viral vector comprises performing particle bombardment.

10. The method of claim 1, wherein introducing the viral vector comprises performing a direct DNA transfer into pollen.

11. The method of claim 1, wherein introducing the viral vector comprises performing hand inoculation of an upper surface of a leaf, a mechanical inoculation of a plant bed, a high pressure spray of a leaf, or a vacuum infiltration.

12. The method of claim 1, wherein regenerating the transformant host cell comprises:
   a) growing a transformant host cell in the presence of a selection medium that induces the generation of shoots in the plant species being transformed, thereby providing a transformant shoot;
   b) transferring the transformant shoot to an appropriate root-inducing medium comprising the selection agent, and rooting the transformant shoot to form a plantlet; and
   c) growing the plantlet in soil.

* * * * *